US006749856B1

(12) United States Patent
Berzofsky et al.

(10) Patent No.: US 6,749,856 B1
(45) Date of Patent: Jun. 15, 2004

(54) MUCOSAL CYTOTOXIC T LYMPHOCYTE RESPONSES

(75) Inventors: Jay A. Berzofsky, Bethesda, MD (US); Igor M. Belyakov, Gaithersburg, MD (US); Michael A. Derby, Germantown, MD (US); Brian L. Kelsall, Washington, DC (US); Warren Strober, Bethesda, MD (US)

(73) Assignee: The United States of America, as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/508,552

(22) PCT Filed: Sep. 11, 1998

(86) PCT No.: PCT/US98/19028

§ 371 (c)(1),
(2), (4) Date: Jun. 12, 2000

(87) PCT Pub. No.: WO99/12563

PCT Pub. Date: Mar. 18, 1999

Related U.S. Application Data

(60) Provisional application No. 60/074,894, filed on Feb. 17, 1998, and provisional application No. 60/058,523, filed on Sep. 11, 1997.

(51) Int. Cl.$^7$ .............................................. A61K 39/21
(52) U.S. Cl. ............................... 424/188.1; 424/208.1; 424/434; 424/435; 424/436; 530/324; 530/826
(58) Field of Search ................................. 530/324, 826; 424/184.1, 185.1, 188.1, 208.1, 434, 435, 436

(56) References Cited

U.S. PATENT DOCUMENTS

| 4,629,783 A | 12/1986 | Cosand ...................... 530/324 |
| 4,943,628 A | 7/1990 | Rosen et al. ................ 530/326 |
| 5,030,449 A | 7/1991 | Berzofsky et al. ............ 424/88 |
| 5,081,226 A | 1/1992 | Berzofsky et al. .......... 530/324 |

FOREIGN PATENT DOCUMENTS

| EP | 0 273 716 | 12/1987 |
| WO | WO 87/07616 | 12/1987 |
| WO | WO 94/26785 | 11/1994 |

OTHER PUBLICATIONS

Belyakov et al., "Mucosal Aids Vaccine Reduces Diseases And Viral Load in Gut Reservior And Blood After Mucosal Infection Of Macaques," *Nature Medicine* 7 (12): 1320–1326 (2001).

Ahlers et al., "Construction of an HIV–1 Peptide Vaccine Containing a Multideterminant Helper Peptide Linked to a V3 Loop Peptide 18 Inducing Strong Neutralizing Antibody Responses in Mice of Multiple MHC Haplotypes after Two Immunizations," *J. Immunol.* 150:5647–5665, 1993.

Ahlers et al., "Candidate HIV Type 1 Multideterminant Cluster Peptide–P18MN Vaccine Constructs Elicit Type 1 Helper T Cells, Cytotoxic T Cells, and Neutralizing Antibody, all Using the Same Adjuvant Immunization," *AIDS Res. Hum. Retroviruses* 12:259–272, 1996.

Ahlers et al., "Cytokine–in–Adjuvant Steering of the Immune Response Phenotype to HIV–1 Vaccine Constructs," *J. Immunol.* 158:3947–3958, 1997.

Ahlers et al., "Enhanced Immunogenicity of HIV–1 Vaccine Construct by Modification of the native Peptide Sequence," *Proc. Natl. Acad. Sci. USA* 94:10856–10861, 1997.

Belyakov, et al., "Mucosal Immunization with HIV–1 Peptide Vaccine Induces Mucosal and Systemic Cytotoxic T Lymphocytes and Protective Immunity in Mice Against Intrarectal Recombinant HIV–Vaccinia Challenge," *Proc. Nat. Acad. Sci.* 95:1709–1714, 1998.

Berzofsky et al., "construction of Peptides Encompassing Multideterminant Clusters of Human Immunodeficiency Virus Envelope to Induce In Vitro T Cell Responses in Mice and Humans of Multiple MHC Types," *J. Clinical Invest.* 88:876–884, 1991.

Berzofsky and Berkower, "Novel Approaches to Peptide and Engineered Protein Vaccines for HIB Using Defined Epitopes: Advances in 1994–1995," *AIDS* 1995 9(A):S143–S157, 1995.

Bomsel, M., "Transcytosis of Infectious Human Immunodeficiency Virus Across a Tight Human Epithelial Cell Line Barrier," *Nature Medicine* 3:42–47, 1997.

Butini et al., "Comparative Analysis of HIV–Specific CTL Activity in Lymphoid Tissue and Peripheral Blood," *J. Cellular Biochemistry Abstract Supplement*:147, 1994.

Cranage et al., "Macaques Infected with Live Attenuated SIVmac are Protected Against Superinfection via the Rectal Mucosa," *Virology* 229:143–154, 1997.

di Tommaso et al., "Induction of Antigen–Specific Antibodies in Vaginal Secretions by Using a Nontoxic Mutant of Heat–Labile Enterotoxin as a Mucosal Adjuvant," *Infection and Immunity*, 44:974–979, 1996.

Douce et al., "Intranasal Immunogenicity and Adjuvanticity of site–directed mutant derivatives of cholera toxin," *Infection and Immunity* 65:2821–2828, 1997.

Gallichan, et al., "long–Lived Cytotoxic T Lymphocyte Memory in Mucosal Tissues After Mucosal but not Systemic Immunization," *J. Exp. Med.* 184:1879–1890, 1996.

Graham et al., "Candidate AIDS Vaccines," *New England Journal of Medicine* 333:1331–1339, 1995.

Hale et al., "T Cell Multideterminant Regions in the Human Immunodeficiency Virus Envelope: Toward Overcoming the Problem of Major Histocompatibility Complex Restriction," *International Immunology* 1:409–415, 1989.

(List continued on next page.)

*Primary Examiner*—Jeffrey Stucker
(74) *Attorney, Agent, or Firm*—Towsend and Towsend and Crew LLP

(57) ABSTRACT

The invention provides methods for induction of an antigen-specific, mucosal cytotoxic T lymphocyte response useful in preventing and treating infections with pathogens that gain entry via a mucosal surface.

40 Claims, 17 Drawing Sheets

OTHER PUBLICATIONS

Haynes, B.F., "Scientific and Social Issues of Human Immunodeficiency Virus Vaccine Development," *Science* 260:1279–1286, 1993.

Klavinskis et al., "Mucosal or Targeted Lymph Node Immunization of Macaques with a Particulate SIVp27 Protein Elicits Virus–Specific CTL in the Genito–Rectal Mucosa and Draining Lymph Nodes," *J. Immunol.* 157:2521–2527, 1996.

Kozlowski et al., "Serum Angiotensin–1 Converting Enzyme Activity Processes a Human Immunodeficiency Virus 1 Gp160 Peptide for Presentation by Major Histocompatibility Complex Class I Molecules," *J. Exp. Med.* 175:1417–1422, 1992.

Langermann, S., "New Approaches to Mucosal Immunization," *Seminars in Gastrointestinal Disease* 7:12–18, 1996.

Lehner, et al., "Protective Mucosal Immunity Elicited by Targeted Iliac Lymph Node Immunization with a Subunit SIV Envelope and Core Vaccine in Macaques," *Nature Medicine* 2:767–775, 1996.

Miller et al., "Genital Mucosal Transmission of Simian Immunodeficiency Virus: Animal Model for Heterosexual Transmission of Human Immunodeficiency Virus," *J. Virol,* 63:4277–4284, 1989.

Modrow et al., "Computer–Assited Analysis of Envelope Protein Sequences of Seven Human Immunodeficiency Virus Isolates: Prediction of Antigenic Epitopes in Conserved and Variable Regions," *J. Virol.* 61:570–578, 1987.

Musey et al., "HIV–1 Induces Cytotoxic T Lymphocytes in the Cervix of Infected Women," *J. Exp. Med.* 185:293–300, 1997.

Neutra et al., "Antigen Sampling Across Epithelial Barriers and Induction of Mucosal Immune Responses," *Annu. Rev. Immunol.* 14: 275–200, 1996.

Parditos et al., "Antibody Responses to Non–Immunogenic Synthetic Peptides Induced by Co–Immunization with Immunogenic Peptides," *Immunology* 77:262–266, 1992.

Parditos et al., "Mucosal Immunization with a Measles Virus CTL Epitope Encapsulated in Biodegradable PLG Microparticles," *J. Immun. Meth.* 195:135–138, 1996.

Parditos et al., "The Adjuvant Effect of a Non–Toxic Mutant of Heat–Labile Enterotoxin of *Escherichia Coli* for the Induction of Measles Virus–Specific CTL Responses After Intranasal Co–Immunization with a Synthetic Peptide," *Immunology* 89:483–487, 1996.

Porgador et al., "Intranasal Immunization with CTL Epitope Peptides from HIV–1 or Ovalbumin and the Mucosal Adjuvant Cholera Toxin Induces Peptides–Specific CTLs and Protection Against Tumor Development in Vivo," *J. Immunol.* 158:834–841, 1997.

Shirai et al., "Broad Recognition of Cytotoxic T Cell Epitopes from the HIV–1 Envelope Protein with Multiple Class I Histocompatibility Molecules," *J. Immunol.* 148:1657–1667, 1992.

Shirai et al., "Helper–Cytotoxic T Lymphocyte (CTL) Determinant Linkage Required for Priming of Anti–HIV CD8+ CTL in Vivo with Peptide Vaccine Constructs," *J. Immunol.* 152:549–556, 1994.

Takahashi et al., "An Immunodominant Epitope of the Human Immunodeficiency Virus Envelope Glycoprotein Gp 160 Recognized by Class I Major Histocompatibility Complex Molecule–Restricted Murine Cytotoxic T Lymphocytes," *Proc. Natl. Acad. Sci. USA* 85:3105–3109, 1998.

Takahashi et al., "Induction of Broadly Cross–Reactive Cytotoxic T Cells Recognizing an HIV–1 Envelope Determinant," *Science* 255:333–336, 1992.

Takeshita et al., "Molecular Analysis of the Same HIV Peptide Functionally Binding to Both a Class I and a Class II MHC Molecule," *J. Immunol.* 154:1973–1986, 1995.

Yamamoto et al., "Mutants in the ADP–ribosyltransferase Cleft of Cholera Toxin Lack Diarrheagenicity but retain adjuvanticity," *J. Exp. Med.* 185: 1203–1210, 1997.

Yamamoto et al., "A nontoxic mutant of cholera toxin elicits Th2–type responses for enhanced mucosal immunity," *Proc. Natl. Acad. Sci. USA* 94:5267–5272, 1997.

Lee "Acquired Immunodeficiency Disease Vaccines: Design and Development", Chapter 32 AIDS Vaccines in AIDS: Biology, Diagnosis, Treatment and Prevention, fourth edition, edited by Vincent T DeVita, Jr., et al, Lippincott–Raven Publishers, 1997, pp. 605–616.*

Louwagie et al. "Phylogenetic analysis of gag genes from 70 international HIV–1 isolates provides evidence of multiple genotypes", *AIDS*, vol. 7 (1993), pp. 769–780.*

McCutchan et al. "Genetic Analysis of HIV–1 Isolated from Zambia and an Expanded Phylogenetic Tree for HIV–1", *Journal of Acquired Immune Deficiency Syndromes*, vol. 5 (1992), pp. 441–449.*

* cited by examiner

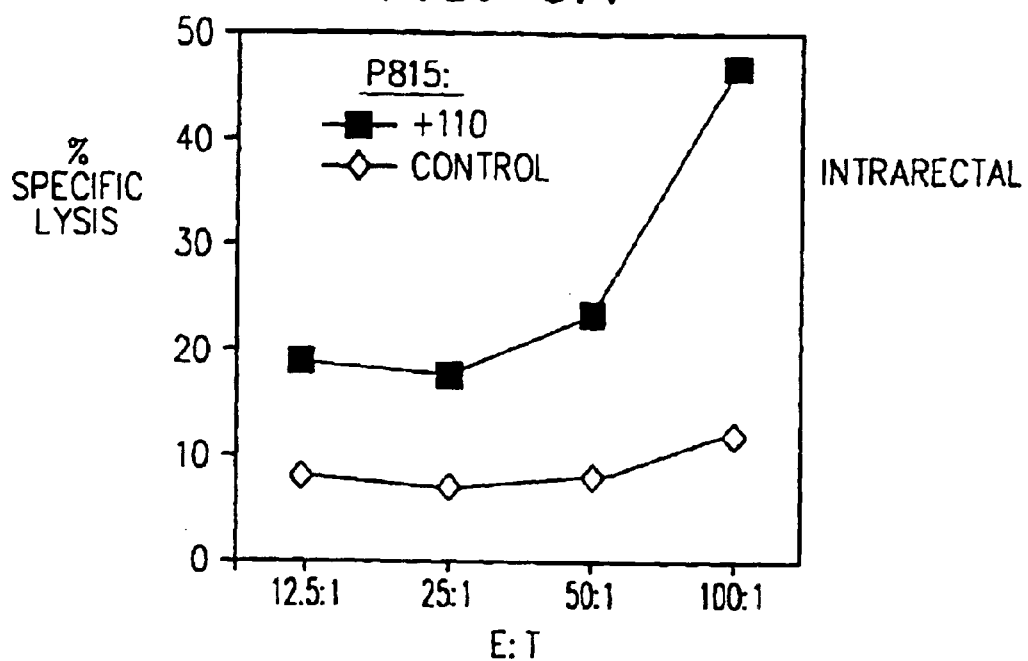
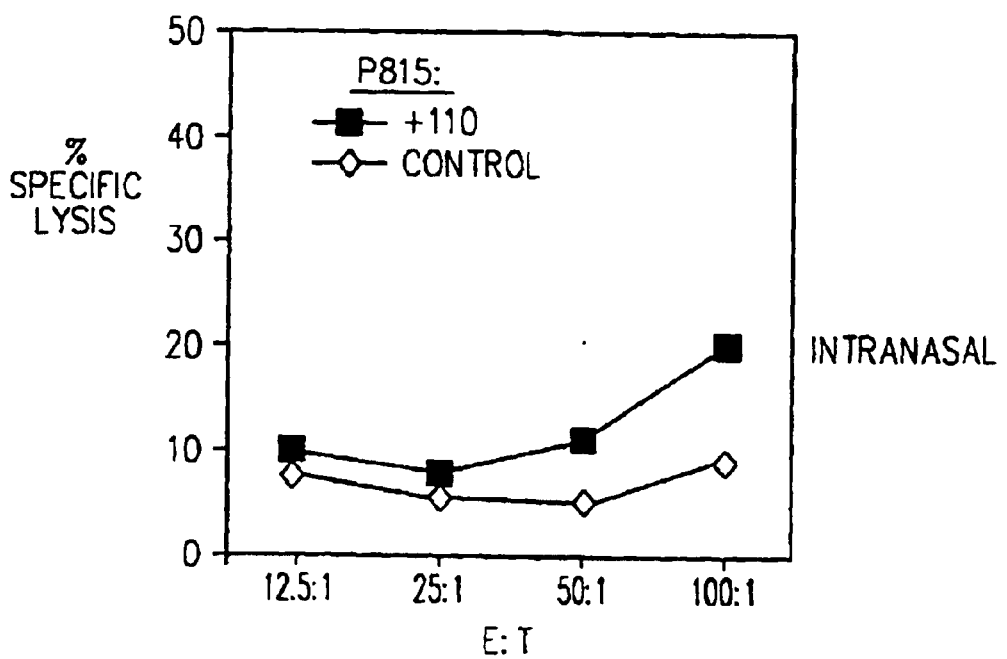

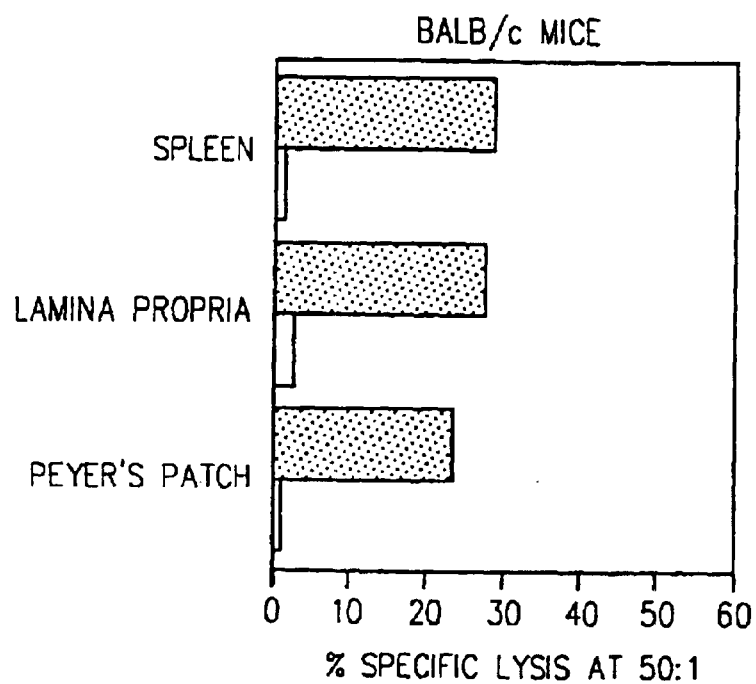
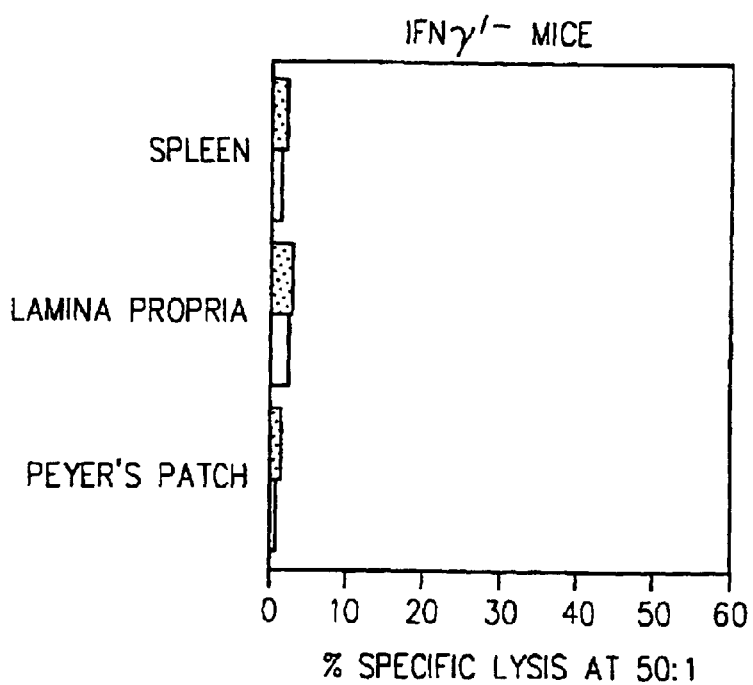

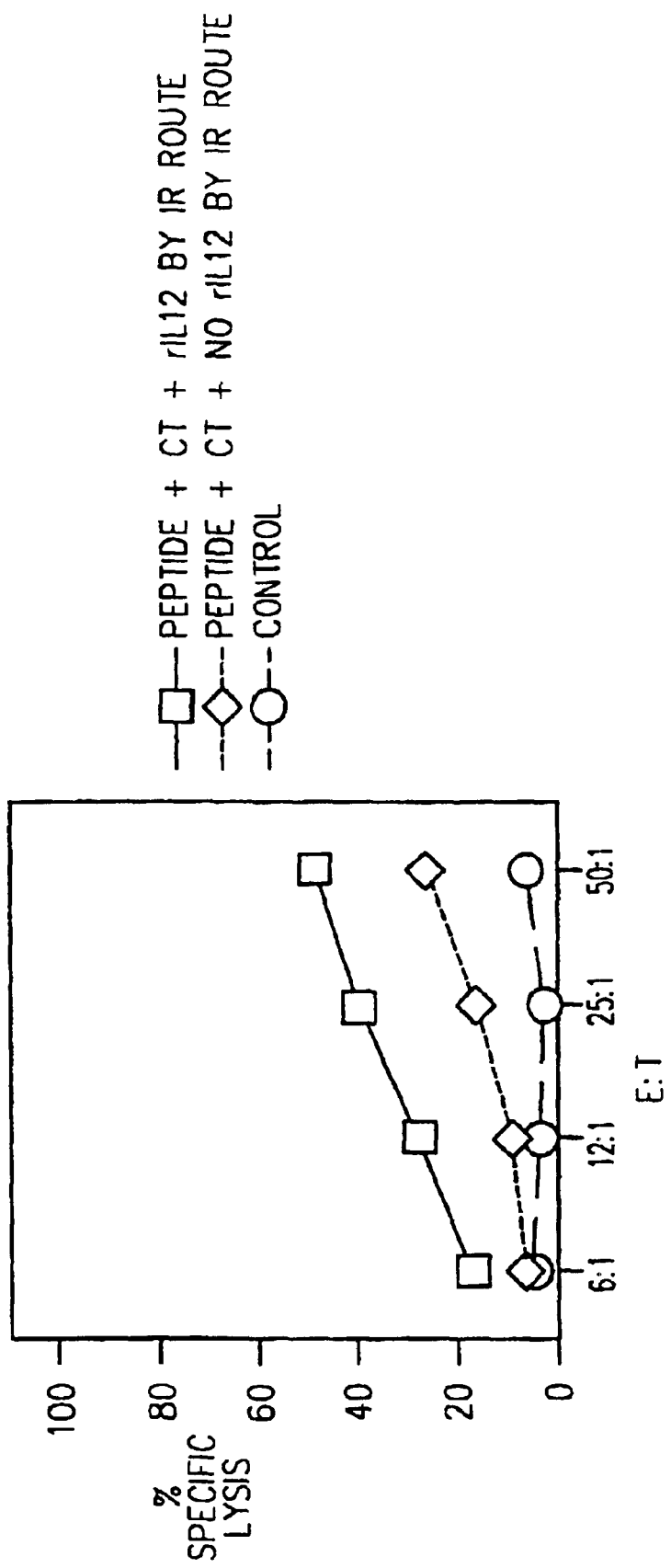

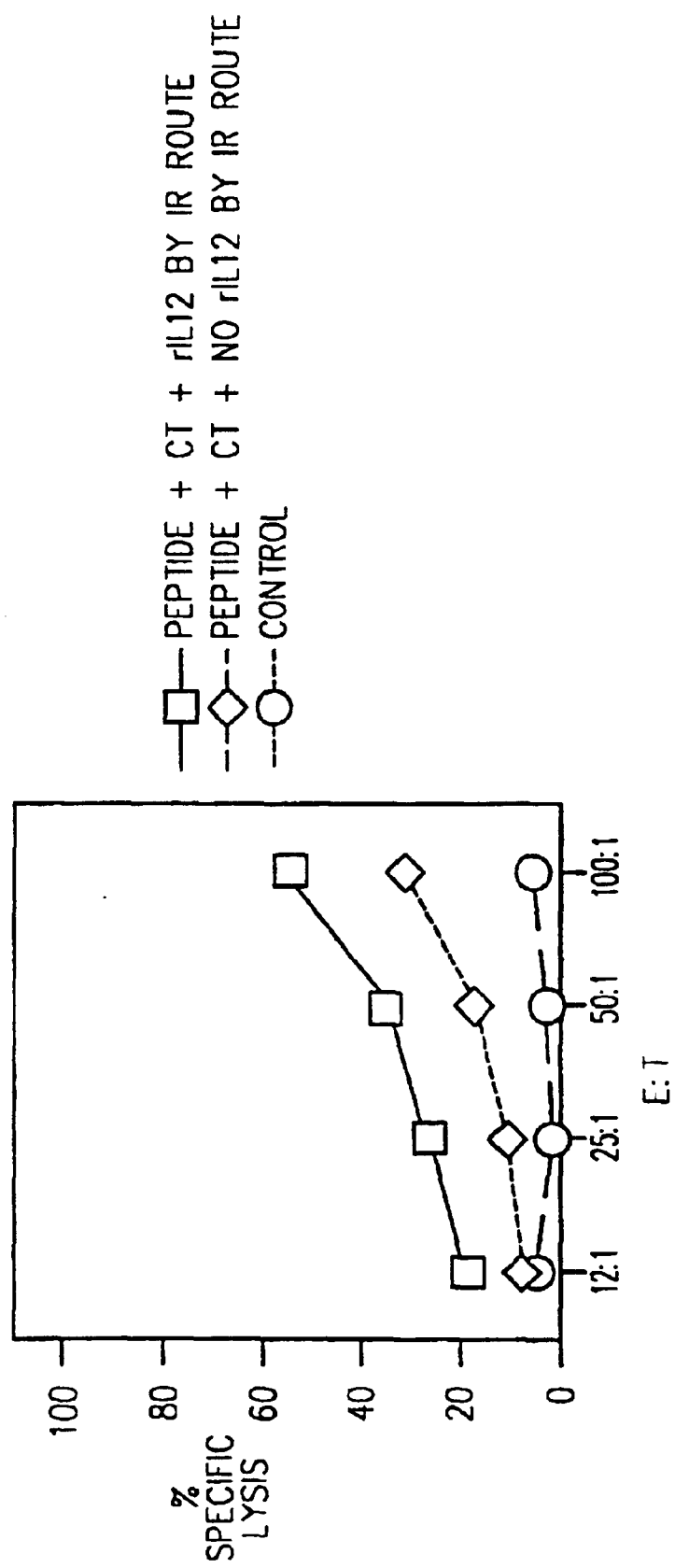

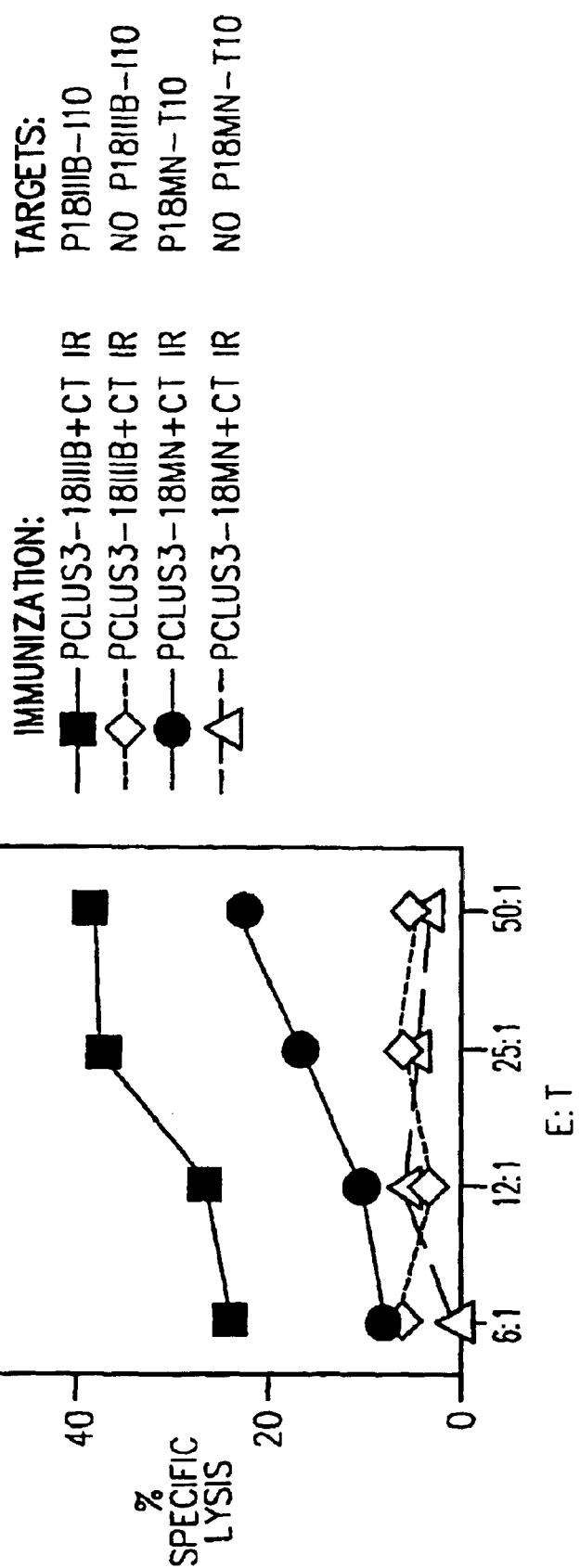

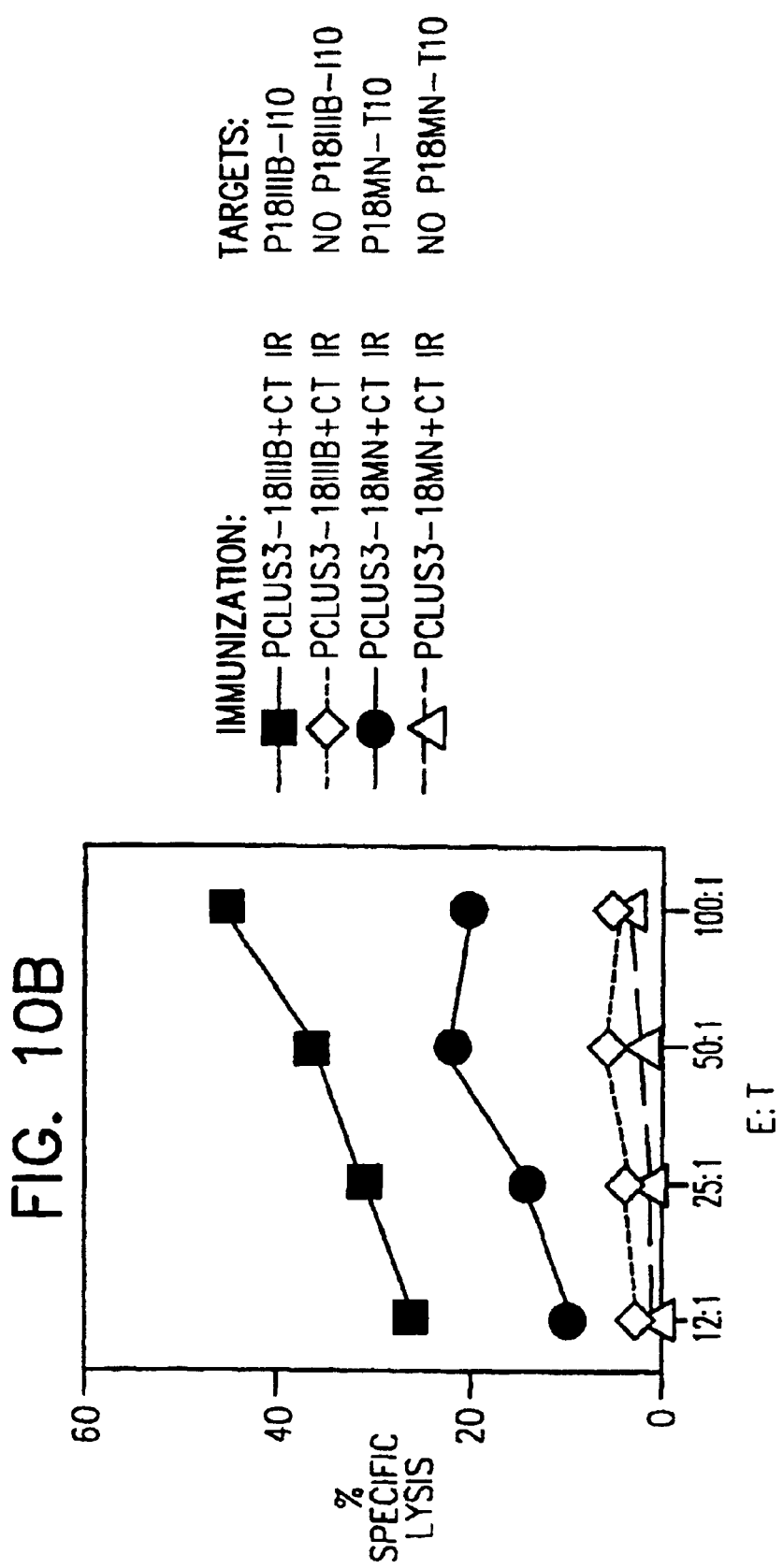

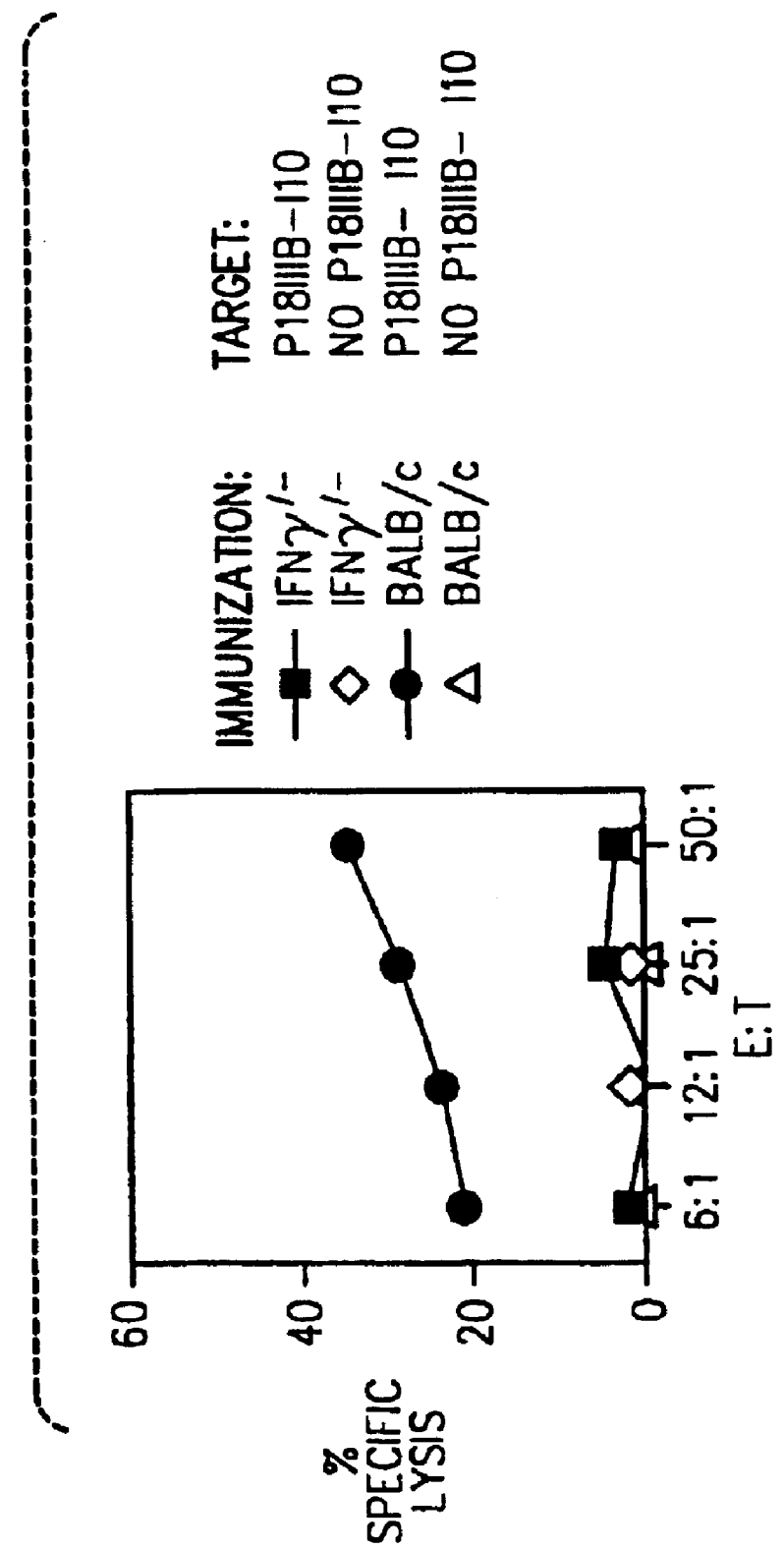

MUCOSAL CYTOTOXIC T LYMPHOCYTE RESPONSES

RELATED APPLICATIONS

The present application is a continuation-in-part application of, and claims the benefit under Title 35 of U.S. Provisional Application Nos. 60/058,523 filed on Sep. 11, 1997, and No. 60/074,894 filed on Feb. 17, 1998.

TECHNICAL FIELD

The present invention relates to methods and compositions for stimulating immune responses in mammals. More particularly, the invention relates to methods and compositions for stimulating mucosal immunity.

BACKGROUND OF THE INVENTION

Many infectious pathogens, e.g., HIV-1, enter their mammalian hosts via a mucosal tissue prior to establishing a systemic infection. Veazey, et al., *Science* 280:427–431, 1998. Accordingly, vaccines capable of protecting against HIV should be capable of inducing long-term mucosal immune responses. A number of recent studies have shown that such immune responses require direct stimulation of mucosal tissues, and may be achieved with live attenuated virus, Cranage, et al., *Virology* 229:143–154, 1997, subunit SIV envelope Lehner, et al., *Nature Medicine* 2:767–775, 1996, HIV-recombinant viruses, including recombinant MVA 89.6 env (Belyakov et al., unpublished), or HIV peptide constructs Belyakov, et al., *Proc. Nat. Acad. Sci.* 95:1709–1714, 1998 (see also, Gallichan, et al., *J. Exp. Med.* 184:1879–1890, 1996; Cranage, et al., *Virology* 229:143–154, 1997; and Rosenthal, et al., *Semin. Immunol.* 9:303–314, 1997).

Numerous questions remain, however, concerning which vaccine candidates may afford the most effective protection against mucosal challenge with virus, and what mechanisms may be involved in mediating protective immunity. While a number of studies have shown a role for CTL in protection against infections such as influenza that have a mucosal component (Taylor and Askonas, *Immunology* 58:417–420, 1986; Epstein et al., *J. Immunol.* 160:322–327, 1998; Kulkarni et al., *J. Virol.* 69:1261–1264, 1995), these reports have not established whether the CTL need to be in a local mucosal site to protect. Conversely, while other studies have shown the induction of CTL in the mucosa, they have not established that these cells have a role in protection (Gallichan and Rosenthal, *J. Exp. Med.* 184:1879–1890, 1996; Bennink et al., Immunology 35:503–509, 1978; Lohman et al., *J. Immunol.* 155:5855–5860, 1995); and Klavinskis, et al., *J. Immunol.* 157:2521–2527, 1996 *J. Immunol.* 155:5855–5860, 1995. Yet other studies have shown the induction by vaccines of protective immunity in the mucosa, but in the face of multiple immune responses, have not been able to sort out which responses are involved in protection (Lehner et al., *Nature Medicine* 2:767–775, 1996; Putkonen et al., *J. Virol.* 71:4981–4984, 1997; Miller et al., *J. Virol.* 71:1911–1921, 1997; Quesada-Rolander et al., *AIDS Res Hwn Retroviruses* 12:993–999, 1996; Bender et al., *J. Virol.* 70:6418–6424, 1996; Wang et al., *Vaccine* 5:821–825, 1997).

Thus, although the role of CTL in protection against mucosal infections has been of interest for decades, especially in the case of influenza virus, prior investigations have failed to identify fundamental mechanisms linking immune responses to protection. In this regard, because mucosal infection by virus induces a local IgA response, it has been too readily assumed that this response, and not a concomitant CTL response, was responsible for protection against viral infection through the mucosal route. However, the role of secretary IgA in neutralizing and protecting against mucosal HIV challenge is also not clear.

CTL are crucial mediators of immunity to intracellular microorganisms such as viruses as well as certain bacteria and protozoan parasites. CTL specifically recognize "non-self" antigenic peptides bound to major histocompatibility complex (MHC) class I molecules on the surface of "target cells" and then kill the target cells expressing the non-self antigenic peptides. Non-self polypeptides from which the non-self peptides are derived can be a) proteins encoded by intracellular microbes, b) host-encoded proteins whose expression is induced by a microbe, or c) mutant host encoded proteins expressed by, for example, tumor cells.

Thus, generation of CTL responses in the inductive and the effector mucosal immune system may be important to establishing effective protective immunity to intracellular microbial pathogens that establish infection via the mucosal barriers. In some cases, administration of antigens via parenteral routes (subcutaneous, intramuscular, intravenous or intraperitoneal, for example) either fails to induce mucosal immunity or does so extremely inefficiently.

As noted above, previous reports of mucosal immune responses elicited by mucosal challenge with viruses have disclosed that the latter induces antiviral antibody responses, and in some cases CTL responses, in the intraepithelial lymphoid populations. Chen et al., *J. Virol.* 71:3431–3436, 1997; Sydora, et al., *Cell Inununol.* 167:161–169, 1996. However, it is not clear if either of such responses is relevant to protection against viral infection in general, or HIV infection in particular. Additional studies have suggested a role for CTL in protection against infections that involve the mucosa, such as influenza or respiratory syncytial virus, Taylor et al., *Immunology* 58:417–420, 1986; Epstein et al., *J. Immunol.* 160:322–327, 1998; Kulkarni et al., *J. Virol.* 69:1261–1264, 1995. However, these studies have not addressed the question of whether CTL must be present at the mucosal site of infection, or if their principal activity occurs systemically.

Accordingly, a need exists in the art to better define the roles and mechanisms of CTL in mediating immunity and to develop new tools for mediating immune protection against HIV and other pathogens, particularly by conferring immune protection at mucosal sites where such pathogens initially proliferate.

SUMMARY OF THE INVENTION

The present invention is directed to methods and compositions for inducing a protective mucosal CTL response in a subject. The methods of the invention involve administering either a soluble antigen itself, or a polynucleotide encoding the soluble antigen, to a mucosal surface. The soluble antigens can be full length, naturally occurring polypeptides or fragments (i.e., peptides) derived from them. Peptides to be administered can be any length less than that of the naturally occurring polypeptide. They can be, for example, five to one hundred amino acid residues long, preferably twenty to seventy five amino acid residues long, more preferably twenty five to sixty amino acid residues long and most preferably thirty to fifty amino acid residues long.

The soluble antigen is administered with an adjuvant at the mucosal site or without an adjuvant. Adjuvants can be, for example, cholera toxin (CT), mutant CT (MCT), *E. coli* heat labile enterotoxin (LT) or mutant LT D1 (MLT). IL-12 and/or IFNγ can be administered with the soluble antigen either in the presence or absence of an adjuvant. Alternatively, the two cytokines (IL-12 and/or IFNγ) can be administered systemically and separately from the soluble antigen which is administered mucosally, optionally with adjuvant. Mucosal routes of administration include IR, intranasal (IN), intragastric (IG), intravaginal (IVG) or intratracheal (IT).

Soluble antigens can be derived from pathogenic viruses (e.g., HIV-1, influenza virus or hepatitis A virus), bacteria (e.g, *Listeria monocytogenes*), protozoans (e.g., *Giardia lamblia*). Alternatively, the soluble antigen can be a tumor-associated antigen, e.g., prostate specific antigen produced by prostate tumor cells or tyrosinase produced by melanoma cells. Peptide antigens can be cluster peptide vaccine constructs (CL WvAC). For example, an HIV-1 CLUVAC can include one or more of the following sequences: EQMHEDIISLWDQSLKPCVKRIQRGPGRAFVTIGK (SEQ ID NO:1), KQIINMWQEVGKAMYAPPISGQIRRIQRGPGRAFVTIGK (SEQ ID NO:2), RDNWRSELYKYKVVKIEPLGVAPTRIQRGPGRAFVTIGK (SEQ ID NO:3), AVAEGTDRVIEVWQGAYRAIRHIPRRIRQGLERRIQRGPGRAFVTIGK (SEQ ID NO:4), DRVIEVVQGAYRAIRHIPRRIRQGLERRIQRGPGRAFVTIGK (SEQ ID NO:5), DRVIEVVQGAYRAIRRIQRGPGRAFVTIGK (SEQ ID NO:6), AQGAYRAIRHIPRRIRRIQRGPGPRAFVTIGK (SEQ ID NO:7), EQMHEDIISLWDQSLKPCVKRIHIGPGRAFYTTKN (SEQ ID NO:8), KQIINMWQEVGKAMYAPPISGQIRRIHIGPGRAFYTTKN (SEQ ID NO:9), RDNWRSELYKYKVVKIEPLGVAPTRIHIGPGRAFYTTKN (SEQ ID NO:10), AVAEGTDRVIEVVQGAYRAIRHIPRRIRQGLERRIHIGPGRAFYTTKN (SEQ ID NO:11), DRVIEVVQGAYRAIRHIPRRIRQGLERRIHIGPGRAFYTTKN (SEQ ID NO:12), DRVIEVVQGAYRAIRRIHIGPGRAFYTTKN (SEQ ID NO:13) or AQGAYRAIRHIPRRIRRIHIGPGRAFYTTKN (SEQ ID NO:14).

Preferably, the CLUVAC includes the amino acid sequence of SEQ ID NO:2, SEQ ID NO:9 or SEQ ID NO:12. Antigenic peptides can be longer than the length specified by the SEQ ID NOS.recited herein, i.e., the peptide can be extended by adding one or more (e.g., 5, 10, 15, 20) amino acids at the amino and/or carboxy termini of the peptide with any given SEQ ID NO.

The invention also encompasses methods for inducing a protective mucosal CTL response in a subject in which the soluble antigen is delivered IR. Preferably, the level of CTL activity induced by IR immunization is at least 10% greater than that induced by other routes of mucosal administration (e.g., IN). More preferably, mucosal CTL activity induced by IR immunization is at least 2-fold, more preferably, at least 5-fold, and most preferably, at least 10-fold greater than that induced by other routes of mucosal immunization (e.g., IN or IG).

Subjects to which the methods of the invention are applied are mammals, e.g., humans, non-human primates, cats or mice.

Also provided within the invention are immunogenic compositions for inducing a protective mucosal CTL response in a subject which are adapted for intrarectal administration. The compositions comprise a purified soluble antigen formulated for intrarectal delivery to the rectum, colon, sigmoid colon, or distal colon. They may be, formulated as a rectal enema, foam, suppository, or topical gel and generally comprise a base, carrier, or absorption-promoting agent adapted for intrarectal delivery.

In more detailed aspects, the immunogenic compositions of the invention may include a rectal emulsion or gel preparation, preferably wherein the soluble antigen is admixed with a homogenous emulsion or gel carrier, eg., a polyoxyethylene gel. Alternatively, the soluble antigen may be admixed with a rectally-compatible foam.

In other preferred aspects, the immunogenic compositions of the invention are formulated in a suppository. The suppository is comprised of a base or carrier specifically adapted for intrarectal delivery of the antigen. Preferred bases may be selected from a polyethyleneglycol, witepsol H15, witepsol W35, witepsol E85, propyleneglycol dicaprylate (Sefsol 228), Miglyol8lo, hydroxypropylcellulose-H (HPC), or carbopol-934P (CP). More preferably, the suppository comprises at least two base materials to optimize structural and delivery performance. In other aspects, the suppository includes a stabilizing agent to minimize intrarectal deradation of the soluble antigen.

To optimize intrarectal delivery, the immunogenic compositions of the invention also preferably include an absorption-promoting agent, for example a surfactant, mixed micelle, enamine, nitric oxide donor, sodium salicylate, glycerol ester of acetoacetic acid, cyclodextrin or beta-cyclodextrin derivative, or medium-chain fatty acid.

In yet additional aspects of the invention, immunogenic compositions are provided which include an adjuvant which enhances the CTL response. Suitable adjuvants are detoxified bacterial toxins, for example detoxified cholera toxin (CT), mutant cholera toxin (MCT), mutant- *E. coli* heat labile enterotoxin, and pertussis toxin. Preferably, the adjuvant is conjugated to a mucosal tissue or T cell binding agent, such as protein A, an antibody that binds a mucosal tissue- or T-cell-specific protein, or a ligand or peptide that binds a mucosal tissue- or T-cell-specific protein. In more preferred aspects, the adjuvant is a recombinant cholera toxin (CT) having a B chain of CT substituted by protein A conjugated to a CT A chain, which exhibits reduced toxicity and enhances mucosal tissue binding mediated by protein A. Alternatively the adjuvant may be conjugated to a protein or peptide that binds specifically to T cells, for example by binding CD4 or CD8 (eg., the HIV V3 loop or a T cell-binding peptide fragment of the HIV V3 loop).

Unless otherwise defined, all technical and scientific terms used herein have the same meaning as commonly understood by one of ordinary skill in the art to which this invention belongs. Although methods and materials similar to those described herein can be used in the practice or testing of the present invention, suitable methods and materials are described below. In case of conflict, the present application, including definitions, will control. In addition, the materials, methods, and examples described herein are illustrative only and not intended to be limiting other features and advantages of the invention, e.g., prevention of viral or other infectious diseases, will be apparent from the following detailed description, from the drawings and from the claims.

BRIEF DESCRIPTION OF THE DRAWINGS

FIG. 6A is a line graph showing the results of a CTL assay using SP cells obtained from animals six months after IR immunization with an antigenic peptide.

FIG. 6B is a line graph showing the results of a CTL assay using SP cells obtained from animals six months after intranasal (IN) immunization with antigenic peptide.

FIG. 8A is a bar graph showing the results of a CTL assay using effector cells from wild-type BALB/c mice.

FIG. 8B is a bar graph showing the results of a CTL assay using effector cells from BALB/c mice which lack the ability to produce functional IFNγ. These experiments show the dependence of IR induction of CTL on IFNγ.

FIG. 9A is a line graph showing the results of a CTL assay using PP as effector cells.

FIG. 9B is a line graph showing the results of a CTL assay using SP cells as effector cells. PP and SP cells were obtained from BALB/c mice thirty five days after IR immunization with either antigenic peptide, CT and IL-12 (composition A) or antigenic peptide and CT (without IL-12; composition B).

FIGS. 10A and 10B demonstrate that IR immunization with PCLUS3-18IIIB or PCLUS3-18MN induces both Peyer's patch (panel A) and spleen (panel B) long-lasting immunity. However the levels of the induction of CTL are different. Killing of P18IIIB-I10 (closed squares) or P18MN-T1O peptide-pulsed targets (closed circles) is compared with killing of unpulsed targets (open squares or circles). In both panel A and panel B, SEM of triplicate were all <5% of the mean.

FIG. 14A depicts induction of the mucosal and systemic CTL responses by different routes of immunization with synthetic peptide HIV vaccine. Killing of peptide-pulsed targets (closed bars) is compared with killing of unpulsed targets (open bars) at an effector-to-target ratio of 50:1. Panel A depicts results or immunizing on day 35 (IR or SC—bar 1, no immunogen; bar 2, SC; bar 3, IR) BALB/c mice challenged intrarectally with 2.5×10$^7$ plaque-forming units (pfu) of vaccinia virus expressing gp 160IIIB.

FIGS. 17A and 17B demonstrate that IL-12 cannot act directly in the induction of mucosal CDB+CTL in the absence of IFNγ. IFNγ$^{-/-}$ mice (BALB/c background) were immunized IR with the rmIL-12 (1 μg/mouse)+DOTAP together with peptide. On day 35 HIV-specific Peyer's patch CTL (FIG. 17A) and spleen CTL (FIG. 17B) were studied. Killing of P18IIIB-I10 pulsed targets by effector cells from immunized IFNγ$^{-/-}$ mice (closed squares) or conventional BALB/c mice (closed circles) is compared with killing of unpulsed targets (open squares or circles).

DETAILED DESCRIPTION

A. Induction of Mucosal Immunity

Figure 1:
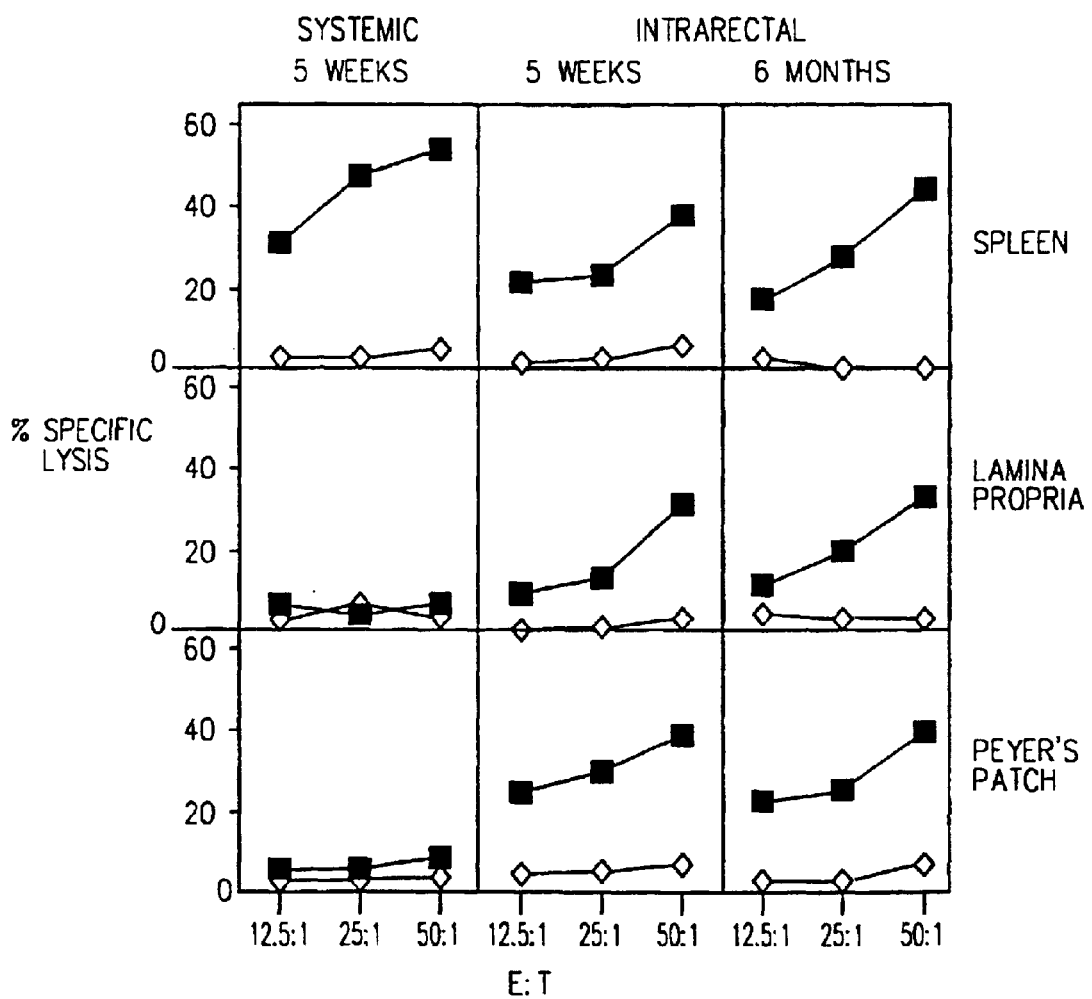
FIG. 1 is a series of line graphs showing the results of a CTL assay. IR HIV-1 peptide immunization induced long lasting mucosal and systemic CTL activity.

The present invention is based on the discovery that IR administration of a peptide, e.g., a synthetic multideterminant HXV-1 gp160 envelope glycoprotein peptide, to a mucosal surface can induce an antigen-specific, protective CTL response in the mucosal immune system, even in the absence of a mucosal adjuvant.

The exemplary synthetic multideterminant peptides (CLUVAC) are composed of subregions containing epitopes that evoke some or all of (a) a helper T cell response, (b) a CTL response and (c) a high titer of neutralizing antibodies in multiple hosts of a given species expressing a broad range of MHC haplotypes. IR immunization with the HIV-1 CLU-VAC PCLUS3-18IIIB (SEQ ID NO:2), and the mucosal adjuvant CT induced peptide-specific CTL in both the inductive (PP) and the effector (LP) sites of the mucosal immune system, as well as in systemic lymphoid tissue, i.e., SP. In contrast, systemic immunization with peptide vaccine produced HIV-1 peptide-specific CTL only in the SP.

IR immunization induced long-lasting protective immune responses. For example, antigen-specific CTL were found in both mucosal and systemic sites 6 months after immunization. IR immunization with the antigenic peptide elicited significantly stronger CTL responses than IN immunization with the same peptide. While IR administration with PCLUS3-18IIIB (SEQ ID NO:2) induced a significant response when administered alone, the response was enhanced by the inclusion of CT. The CTL were CD8+ T lymphocytes restricted by MHC class I molecules, recognizing MHC class I positive target cells either endogenously expressing HIV-1 gp160 or'pulsed with an appropriate gp160 peptide. Induction of both mucosal and systemic CTL response by IR immunization was IL-12dependent, as shown by inhibition of induction of CTL in mice treated i.p. with anti-IL-12 antibody. Furthermore, inclusion of IL-12 in the composition of antigenic peptide and CT used for IR immunization resulted in enhanced mucosal and systemic CTL responses relative to the responses elicited by antigenic peptide and CT without IL-12. The dependence on IFNγ of mucosal and systemic CTL generation following IR inmnunization was demonstrated by the absence of such responses in mice which lack the ability to produce functional IFNγ, e.g., as the result of a premature stop-codon in the IFNγ-encoding gene. The stop-codon mutation causes the gene to encode a truncated protein lacking the activity of IFNγ.

IR immunization with PCLUS3-18IIIB (SEQ ID NO:2) protected mice against an IR challenge with a recombinant vaccinia virus expressing HIV-1 IIIB gp160. Thus, an HIV-1 peptide induced CTL responses in the mucosal and systemic immune systems after IR immunization and protected against mucosal challenge with virus expressing HIV-1 gp160.

The immunization method of the invention is useful to induce a mucosal CTL response to any soluble antigen. Accordingly, the invention provides a new method for vaccine administration to elicit immunologic protection against viruses that enter through mucosal barriers, including HIV-1. The method can also be applied to achieving protection from infection by certain bacteria (e.g., L. monocytogenes) and protozoa (e.g., G. lamblia) that establish infection via mucosae. In addition, since mucosal immunization results in systemic generation of CTL activity, the protocol can also be useful in prevention of infection by microorganisms that enter through non-mucosal routes. The method is also useful for immunotherapy of infections that are mucosally or non-mucosally established. Finally, the methods can be utilized for immunotherapy of cancer, both in the region of and remote from a mucosal surface.

B. Methods of Immunization

The invention features methods for protecting subjects from infection by intracellular microorganisms such as viruses as well as intracellular bacteria and protozoans. The methods involve induction of CTL responses specific for antigenic peptides derived from proteins encoded by genes of relevant microbes and expressed in association with MHC class I molecules on the'surface of infected cells. This is achieved by delivery of an appropriate soluble antigen to a mucosal surface, e.g., rectal, vaginal, nasopharyngeal, gastric or tracheal mucosae. Relevant microorganisms include but are not restricted to those that enter their hosts via mucosal barriers, e.g. HIV-1, influenza virus, enteric viruses such as rotaviruses, hepatitis A virus, papilloma virus, feline immunodeficiency virus, feline leukemia virus, simian immunodeficiency virus, intracellular bacterial pathogens, e.g., L. monocytogenes and mycobacteria such as *M. tuberculosis* and *M. leprae*. Since the responses elicited by mucosal immunization occur in the systemic as well as the mucosal immune system, the methods can also be applied to protection from infection by intracellular pathogens that enter their hosts via non-mucosal (e.g., HIV-1 in some scenarios such as a "stick" by a contaminated syringe needle, rabies virus and malarial protozoans) as well as mucosal routes. In light of the above considerations, immunization via mucosae can also be used for immunotherapy of intracellular infections.

Finally, the mucosal immunotherapy of the invention can be applied to subjects with cancer, particularly, but not limited to, those with solid tumors in the region of the relevant mucosa, e.g., colonic, rectal, bladder, ovarian, uterine, vaginal, prostatic, nasopharyngeal, lung or certain melanoma tumors. Tumor immunity is substantially mediated by CTL with specificity for tumor associated peptides (e.g., prostate specific antigen peptides in prostatic cancer, carcinoembryonic antigen peptides in colon cancer, human papilloma virus peptides in bladder cancer and MART1, gp100 and tyrosinase peptides in melanoma) (Rosenberg et al. (1994) J.N.C.I. 76:1159; Kawakami et al. (1994) Proc. Natl. Acad. Sci. USA. 91:3515) bound to MHC class I molecules on the surface of tumor cells.

B.1 Anticenic Polypeptides

A soluble antigen to be administered according to the invention can be any soluble carbohydrate or peptide antigen, e.g., one containing all or part of the amino acid sequence of a peptide which is naturally expressed in association with a MHC class I molecule on the surface of a cell infected with relevant microbe or expressed on a tumor cell. In the case of infected cells, the cell surface expressed peptide is derived from a protein either encoded by genes of the infectious agent or whose expression is induced by the infectious agent. Thus, the soluble antigen can be a full length, naturally occurring polypeptide, e.g., full length HIV-1 gp160 or gp120 or an antigenic fragment thereof.

Antigen-specific recognition by CTL involves interactions between components of the antigen-specific T cell receptor on the surface of the CTL and residues on both the antigenic peptide and the MHC class I molecule to which the peptide is bound. Thus the soluble antigen can also be a fragment (i.e., a peptide) of the naturally occurring polypeptide that is either (a) itself capable of binding to MHC class I molecules of multiple haplotypes on the surface of antigen presenting cells (APC) and stimulating CD8+ T cell responses in subjects expressing these MHC class I haplotypes or (b) which can be proteolytically processed by APC into fragments with these properties. Ways of establishing the ability of a candidate peptide to stimulate a CTL response in the context of multiple MHC class I haplotypes are well known to one of ordinary skill in the art and are amply described in co-pending U.S. patent application Ser. No. 08/060,988 incorporated herein by reference in its entirety.

Antigenic peptides can be engineered to bind to MHC class II molecules of multiple haplotypes and will be recognized by CD4+ helper T cell precursor cells of subjects expressing multiple MHC class II haplotypes. Ways of establishing the ability of a candidate peptide to stimulate a helper T cell response in the context of multiple MHC class II haplotypes are well known to one of ordinary skill in the art and are amply described in co-pending U.S. patent application Ser. No. 08/060,988 incorporated herein by reference in its entirety.

In addition, antigenic peptides, can contain epitopes that elicit neutralizing antibodies, i.e., those that bind to the relevant microbe or a cell infected with the microbe and neutralize or kill it. Ways of establishing these properties of a candidate peptide are well known to one of ordinary skill in the art and are amply described in copending U.S. patent application Ser. No. 08/060,988 incorporated herein by reference in its entirety.

Antigenic peptides can also elicit antibodies that induce antibody-dependent cellular cytolysis (ADCC) of cells infected by the appropriate microbe or tumor cells expressing at their surface the protein from which the antigenic peptide was derived. ADCC is a protective mechanism by which specialized cells of the immune system (K cells) recognize the Fc portion of IgG antibody molecules bound to the surface of a target cell and lyse the relevant target cell. Sera, or other body fluids such as rectal lavages, from test subjects mucosally immunized with a candidate peptide can be tested for their ability to mediate ADCC by methods known to an ordinary artisan. A standard cell mediated lympholysis (CML) assay is used. Briefly, a source of lymphoid ADCC effector cells (e.g., peripheral blood mononuclear cells (PBMC) or SP cells) is incubated in vitro with target cells expressing the above described cell surface protein in the presence of various dilutions of test sera. Lysis of the target cells, which can be measured by the release of a detectable label ($^{51}$Cr, for is example) from prelabeled target cells, is an indication of the presence of ADCC inducing antibodies in the test serum.

Peptides of the invention can be cluster peptide vaccine constructs (CLUVAC). A CLLTVAC is a chimeric peptide containing a) a subregion with multiple overlapping helper T cell activating epitopes that can be presented by multiple MHC class II molecules (a cluster peptide), b) a subregion with a CTL activating epitope and c) a subregion that elicits the production of a neutralizing antibody. The peptide sequences containing these epitopes can be derived from different parts of a microbial or tumor associated polypeptide. Alternatively, the CTL inducing and antibody neutralizing epitopes can be located in one subregion of an antigen and the helper epitope(s) can be in a second subregion. CLUVAC and their design are extensively described in co-pending U.S. patent application Ser. No. 08/060,988 incorporated herein by reference in its entirety.

HIV-1 CLUVAC can include the following sequences: EQMHEDIISLWDQSLKPCVKRIQRGPGRAFVTIGK (SEQ ID NO:1) KQIINMWQEVGKAMYAPPISGQIR-RIQRGPGRAFVTIGK (SEQ ID NO:2) RDNWRSE-LYKYKYKIEPLGVAPTRIQRGPGRAFVTIGK (SEQ ID NO:3) AVAEGTDRVIEVWQGAYRAIRHIPRR-IRQGLERRIQRGPGRAFVTIGK (SEQ ID NO:4) DRVIEVVQGAYRAIRHIPRRIRQGLERRIQRGP-GRAFVTIGK (SEQ ID NO:5) DRVIEVVQGAYRAI-RRIQRGPGRAFVTIGK (SEQ ID NO:6) AQGAYRAI-RHIPRRIRRIQRGPGRAFVTIGK (SEQ ID NO:7) EQM-HEDIISLWDQSLKPCVKRIHIGPGRAFYTTKN (SEQ ID NO:8) KQIINMWQEVGKAMYAPPISGQIRRI-HIGPGRAFYTTKN (SEQ ID NO: 9) RDNWRSE-LYKYKVVKIEPLGVAPTRIHIGPGRAFYTTKN (SEQ ID NO:10) AVAEGTDRVIEVVQGAYRAIRHIPRR-IRQGLERRIHIGPGRAFYTTKN (SEQ ID NO:11) DRVIEVVQGAYRAIRHIPRRIRQGLERRIHIGPG-RAFYTTKN (SEQ ID NO:12) DRVIEVVQGAYRAIRRI-HIGPGRAFYTTKN (SEQ ID NO:13) AQGAYRAI-RHIPRRIRRIHIGPGRAFYTTKN (SEQ ID NO:14)

It is possible, for example, to link a particular cluster peptide to any peptide containing a CTL and/or neutralizing antibody epitope. Examples of cluster peptides include: cluster peptide 1 whose amino acid sequence (EQMHEDIISLWDQSLKPCVK) (SEQ ID NO:17) is the first 20 amino acids of the HIV-1 CLUVAC with SEQ ID NO:1; cluster peptide 3 whose amino acid sequence (KQIINMWQEVGKAMYAPPISGQIR) (SEQ, ID NO:18) is the first 24 amino acids of the HIV-1 CLUVAC with SEQ ID NO: 2; cluster peptide 4 whose amino acid sequence (RDNWRSELYKYKVVKIEPLGVAPT) (SEQ ID NO:19) is the first 24 amino acids of the HIV-1 CLUVAC with SEQ ID NO:3; and cluster peptide 6 whose amino acid sequence (AVAEGTDRVIEWQGAYRAIRHIPRRIRQGLER) (SEQ ID NO:20) is the, first 33 amino acids of the HIV-1 CLUVAC with SEQ ID NO:4.

Of particular interest are peptides containing the amino acid sequences of SEQ ID NO:2, SEQ ID NO:9 and SEQ ID NO:12. Mucosal responses to the first (PCLUS3-18IIIB) are extensively characterized in the Examples presented infra. PCLUS3-18MN (SEQ ID NO:9) and PCLUS6.1-18MN (SEQ ID NO:12) have been tested in human clinical trials. The CTE epitope within PCLUS3-18IIIB (SEQ ID NO:2) is the amino acid sequence RIQRGPGRAFVTIGK (SEQ ID NO:15).

In some instances, mucosal adjuvants are co-administered at the mucosal tissue site with the soluble antigens. Such adjuvants include, but are not limited to, detoxified bacterial toxins, for example detoxified cholera toxin (CT), *E. coli* heat labile toxin (LT), mutant CT (MCT) (Yamamoto et al. *J. Exp. Med.* 185:1203 (1997); Yamamoto et al. *Proc. Natl. Acad. Sci. USA* 58:5267 (1997); Douce et al. Infect. Immunity 65:2821 (1997)), mutant *E. coli* heat labile toxin (MLT) (Di Tommaso et al. *Infect. Immunity* 64:974 (1996) Partidos et al. *Immunology* 89:83 (1996), and pertussis toxin. MCT and MLT contain point mutations that substantially ablate toxicity without substantially compromising adjuvant activity relative to that of the parent molecules. In other preferred embodiments, the adjuvant is modified for increased binding to mucosal tissues and/or T-cells. Thus, in one aspect of the invention, CT or other bacterial toxins are conjugated to a mucosal tissue binding agent, such as protein A, an antibody that binds a mucosal tissue- or T-cell-specific protein (eg., a receptor), or a ligand or peptide that binds a mucosal tissue- or T-cell-specific protein (eg., CD4 or CD8). For example, the B chain of CT may be substituted by protein A, conjugated to the CT A chain, to eliminate toxicity and enhance mucosal tissue binding mediated by protein A. Alternatively, the HIV V3 loop which binds CD4 on T cells may be conjugated to the adjuvant to enhance delivery to T cells.

The CTL augmenting cytokines, eg., IL-12 and IFNγ, are, in some instances, either administered systemically or, preferably, coadministered at the mucosal tissue site with the soluble antigen.

Variants of disclosed antigenic peptides can contain different amino acids (preferably conservative changes) from the parental molecules but retain the biological activity of the parental molecules, e.g., the ability to induce specific CTL responses subsequent to mucosal immunization. Such variants can be synthesized by standard means, and are readily tested in assays known to those in the art. Antigenic polypeptides are typically longer than the length of the nominal SEQ ID NOS. recited herein, i.e., the polypeptide can be extended by adding amino acids to the amino or carboxy termini of the peptide defined by any given SEQ ID NO.

Peptides and polypeptides of the invention will also include those described above but modified for in vivo use by:

(a) chemical or recombinant DNA methods to include mammalian signal peptides (Lin et al., *J. Biol. Chem.* 270:14255 (1995)) or the bacterial peptide, penetratin (Joliot et al., *Proc. Natl. Acad. Sci. USA* 88:1864 (1991)), that will serve to direct the peptide across cell and cytoplasmic membranes and/or traffic it to the endoplasmic reticulum (ER) of antigen presenting cells (APC), e.g., dendritic cells which are potent CTL inducers;

(b) addition of a biotin residue which serves to direct the polypeptides or peptide across cell membranes by virtue of its ability to bind specifically to a translocator present on the surface of cells (Chen et al., *Analytical Biochem.* 227:168 (1995));

(c) addition at either or both the amino- and carboxy-terminal ends, of a blocking agent in order to facilitate survival of the relevant polypeptide or peptide in vivo. This can be useful in those situations in which the termini tend to be degraded ("nibbled") by proteases prior to cellular or ER uptake. Such blocking agents can include, without limitation, additional related or unrelated peptide sequences that can be attached to the amino and/or carboxy terminal residues of the polypeptide or peptide to be administered. This can be done either chemically during the synthesis of the peptide or by recombinant DNA technology (see Section 3.3 infra). Alternatively, blocking agents such as pyroglutamic acid or other molecules known to those of average skill in the art can be attached to the amino and/or carboxy terminal residues, or the amino group at the amino terminus or carboxyl group at the carboxy terminus replaced with a different moiety. Likewise, the polypeptides or peptides can be covalently or noncovalently coupled to pharmaceutically acceptable "carrier" proteins prior to administration.

Also of interest are peptidomimetic compounds based upon the amino acid sequence of the peptides of the invention. Peptidomimetic compounds are synthetic compounds having a three-dimensional structure (i.e. a "peptide motif") based upon the three-dimensional structure of a selected peptide. The peptide motif provides the peptidomimetic compound with the activity of binding to MHC molecules of multiple haplotypes and activating $CD8^+$ and $CD4^+$ T cells from subjects expressing such MHC molecules that is the same or greater than the activity of the peptide from which the peptidomimetic was derived. Peptidomimetic compounds can have additional characteristics that enhance their therapeutic application such as increased cell permeability, greater affinity and/or avidity and prolonged biological half-life. The peptidomimetics of the invention typically have a backbone that is partially or completely non-peptide, but with side groups identical to the side groups of the amino acid residues that occur in the peptide on which the peptidomimetic is based. Several types of chemical bonds, e.g. ester, thioester, thioamide, retroamide, reduced carbonyl, dimethylene and ketomethylene bonds, are known in the art to be generally useful substitutes for peptide bonds in the construction of protease-resistant peptidomimetics.

B.2 In vivo Methods to Deliver Soluble Antigens to Mucosae of a Subject

In methods of the invention that induce mucosal CTL responses, a soluble antigen is delivered to antigen presenting cells of the inductive mucosal immune system (e.g., PP of the intestine). Delivery involves administering to a subject either the soluble antigen itself, e.g., an antigenic peptide, an expression vector encoding the soluble antigen, or cells transfected or transduced with the vector.

B.2.1 Administration of Soluble Antigen

Soluble antigens can be delivered to the mucosal immune system of a mammal using techniques substantially the same as those described infra for delivery to human subjects. Examples of appropriate mammals include but are not restricted to humans, non-human primates, horses, cattle, sheep, dogs, cats, mice, rats, guinea pigs, hamsters, rabbits and goats.

A soluble antigen of the invention can be delivered to the mucosal immune system of a human in its unmodified state, dissolved in an appropriate physiological solution, e.g., physiological saline. Alternatively, it can be modified as detailed in Section B.1 in order to facilitate transport across cell and/or intracellular membranes and to prevent extracellular or intracellular degradation. Its transport across biological membranes can also be enhanced by delivering it encapsulated in liposomes using known methods (Gabizon et al., *Cancer Res.* 50:6371 (1990); Ranade, *J. Clin. Pharmacol.* 29:685 (1989)) or an appropriate biodegradable polymeric microparticle (also referred to as a "microsphere", "nanosphere", "nanoparticle, or "microcapsule"). Naturally, it is desirable that the soluble antigens be selectively targeted to the mucosae. This can be achieved by contacting the soluble antigens directly with the relevant mucosal surface, e.g., by IR, IVG, IN, intrapharyngeal (IPG) or IT infusion or implantation. CTL activity (systemic or mucosal) induced by IR immunization can be two-fold, preferably five-fold, more preferably twenty-fold, even more preferably fifty-fold and most preferably two hundred-fold greater than that induced by IN immunization.

Soluble antigens of the invention can be delivered in liposomes into which have been incorporated ligands for receptors on relevant cells (e.g., dendritic cell or macrophage APC) or antibodies to cell-surface markers expressed by these cells. Thus, for example, an antibody specific for a dendritic cell surface marker can direct liposomes containing both the anti-dendritic cell antibody and the relevant soluble antigen to dendritic cells.

The soluble antigens can be administered mucosally either alone or together with a mucosal adjuvant. Suitable adjuvants include, but are not restricted to, CT, MCT and MLT. IL-12 and/or IFNγ can also be administered to the subject. Thus, a soluble antigen can be administered with an adjuvant, with IL-12 (in the absence of an adjuvant), with IFNγ (in the absence of an adjuvant), with both IL-12 and IFNγ (in the absence of an adjuvant), with an adjuvant and IL-12, with an adjuvant and IFNγ, or with an adjuvant and both IL-12 and IFNγ. The IL-12 and IFNγ can be administered systemically or co-administered mucosally with the peptide. When the soluble antigen is administered encapsulated in liposomes or microparticles, the IL-12 and/or IFNγ can be co-incorporated into the same liposomes/microparticles or incorporated into separate liposomes/microparticles. Alternatively, the cytokines can be administered in a free, soluble form. Examples of other cytokines that can be used, singly or in combination, are granulocyte-macrophage colony-stimulating factor (GM-CSF), interleukin-2 (IL-2), interleukin-7 (IL-7), or tumor necrosis factor a (TNFa). These and other immunopotentiating cytokines are administered as discussed above for IL-12 and IFNγ. Administration can be single or multiple (two, three, four, five, six, eight or twelve administrations, for example). Where multiple, they can be spaced from one day to one year apart. When using peptides without a helper T-cell epitope,it can be necessary to carry out such multiple administrations.

In preferred aspects of the invention formulations of soluble antigen are prepared for intrarectal administration (i.e., delivery to the rectum, colon, sigmoid colon, or distal colon), eg., by formulating the soluble antigen in a rectal enema, foam, suppository, or topical gel. These rectal delivery formulations are adapted for improved delivery, stability, and/or absorption in the rectum, eg., by combining the soluble antigen with one or more known intrarectal delivery base or carrier materials, intrarectal absorption-promoting materials, and/or stabilizers.

Preferred base formulations for rectal delivery of soluble antigen within the methods of the invention include hydrophilic and hydrophobic vehicles or carriers such as those commonly used in formulating suppositories and rectal emulsion or gel preparations. Thus, emulsion vehicles are used which incorporate soluble antigen in an oil/water emulsion suitable for intrarectal administration. Alternatively, gel formulations are provided which incorporate the soluble antigen in a homogenous gel carrier, for example a polyoxyethylene gel such as polyoxyethylene(20) cetylether(BC-20TX). When the antigen is formulated in a rectally compatible foam, a non-CFC propellant foam is preferred.

Preferred carriers or delivery vehicles for use within the invention are conventional suppository base materials that are adapted for intrarectal use, such as polyethyleneglycols. Exemplary polyethyleneglycols known and available in art include PEG 400, PEG 1500, PEG 2000, PEG 4000 or PEG 6000. Preferred bases in this context include witepsol H15, witepsol W35, witepsol E85. These are selected for their desired lipophilic and/or hydrophilic properties, and are often selected to form a multiple layer suppository with both lipophilic and hydrophilic base layers. Preferred lipophilic base materials are macregls of low molecular weight. Particular examples of suitable lipophilic bases include propyleneglycol dicaprylate (Sefsol 228) and Miglyol810. A preferred hydrophilic base is PEG, eg., PEG 400. In one formulation useful within the invention, hydroxypropylcellulose-H (HPC) and/or carbopol-934P (CP) are used as bases for an inner suppository layer, and a witepsol base is used for the outer layer.

Crystalline cellulose or other common stabilizing agents can be added in selected amounts (eg., 30–60% by weight) to the base to promote sustained release.

Selection of base materials, stabilizers, and absorption-promoting agents for formulating intrarectal delivery compositions, particularly suppositories, is determined according to conventional methods, eg., based on melting and drop rates, breaking hardness, disintegration and special breaking times, spreading properties, and diffusion rates. Preferred values of these various properties are known and can be readily determined to adjust antigen formulations to be suitable for intrarectal use. In particular, appropriate values for formulating a time-release suppository having appropriate structural and chemical properties for rectal delivery are known or readily ascertained. In this context, conventional additives, eg., softeners such as neutral oils, Estasan, etc. may be included to optimize consistency, rate of delivery and other characteristics of the formulation.

In formulating mucosal delivery compositions, it is also desired to include absorption-promoting agents to enhance delivery of the soluble antigen and, optionally the CTL-stimulatory cytokine, to the mucosal surface. A variety of absorption promoting agents (i.e., agents which enhance release or diffusion of the antigen and/or CTL-stimulatory cytokine from the delivery vehicle or base, or enhance delivery of the antigen and/or CTL-stimulatory cytokine to the mucosal tissue or T-cells, for example by enhancing membrane penetration) are known in the art and are useful in mucosal delivery formulations of the invention, eg., for inclusion in intrarectal delivery formulations, particularly suppositories. These include, but are not limited to, surfactants (eg., tween 80), mixed micelles, enamines, nitric oxide donors (eg., S-nitroso-N-acetyl-DL-penicillamine, NOR1, NOR4—which are preferably co-administered with an NO scavenger such as carboxy-PITO or doclofenac sodium), sodium salicylate, glycerol esters of acetoacetic acid (eg., glyceryl-1,3-diacetoacetate or 1,2-isopropylideneglycerine-3-acetoacetate) and other release-diffusion/absorption-promoting agents adapted for mucosal delivery.

Absorption-promoting agents useful within the invention include a variety of compounds specifically adapted for intrarectal use. In this context, the rate and extent of rectal drug absorption are often lower than with oral absorption, possibly an inherent factor owing to the relatively small surface area available for drug uptake. In addition, the composition of rectal formulations (solid vs liquid, nature of the suppository base) is an important factor in the absorption process. This relationship between formulation and drug uptake has been clearly demonstrated. Thus, coadministration of absorption-promoting agents (eg., surfactants, sodium salicylate, enamines) represents a key approach towards optimizing rectal drug absorption.

Rectal drug delivery in a site- and rate-controlled manner using suppositories, enemas, osmotic pumps, or hydrogel formulations provides a range of options for manipulating mucosal delivery, eg., controlling concentrations, time-release, and immunogen-drug effects. Absorption from aqueous and alcoholic solutions may occur very rapidly, but absorption from suppositories is generally slower and very much dependent on the nature of the suppository base, the use of surfactants or other additives, particle size of the active ingredients, etc.

Accordingly, preferred formulations for administering soluble antigens and CTL-stimulatory cytokines within the methods of the invention are designed to optimize mucosal delivery. These agents may thus include cyclodextrins and beta-cyclodextrin derivatives (e.g., 2-hydroxypropyl-beta-cyclodextrin and heptakis(2,6-di-O-methyl-beta-cyclodextrin). These compounds, preferably conjugated with one or more of the active ingredients and formulated in an oleaginous base, are well documented to enhance bioavailability in intrarectal formulations. Other absorption-enhancing agents adapted for intrarectal delivery include medium-chain fatty acids, including mono- and diglycerides (e.g., sodium caprate-extracts of coconut oil, Capmul), and triglycerides (e.g., amylodextrin, Estaram 299, Miglyol 810).

It is well known in the medical arts that dosages for any one human subject depend on many factors, as well as the particular compound to be administered, the time and route of administration and other drugs being administered concurrently. Dosages for the soluble antigens of the invention will vary, but can be approximately 0.01 mg to 100 mg per administration. Dosages for the mucosal adjuvants will be approximately 0.001 mg to 100 mg per administration. Dosages for IL-12 will be approximately 25 $\mu$g/kg to 500 $\mu$g/kg and for IFN$\gamma$ will be 300 KU to 30,000 KU per administration—comparable dosages will be used for other cytokines. For example, 3,000 KU of IFN$\gamma$ can be administered to a human patient once per week. Methods of determining optimal doses are well known to pharmacologists and physicians of ordinary skill. Routes will be, as recited supra, mucosal, e.g., IR, IG, IVG, IN, IPG or IT.

B.2.2 Administration of Soluble Antigens Utilizing Expression Vectors Encoding the Soluble Antigens.

An expression vector is composed of or contains a nucleic acid in which a polynucleotide sequence encoding a peptide or polypeptide of the invention is operatively linked to a promoter or enhancer-promoter combination. A promoter is a trancriptional regulatory element composed of a region of a DNA molecule typically within 100 nucleotide pairs upstream of the point at which transcription starts. Another transcriptional regulatory element is an enhancer. An enhancer provides specificity in terms of time, location and expression level. Unlike a promoter, an enhancer can function when located at variable distances from the transcription site, provided a promoter is present. An enhancer can also be located downstream of the transcription initiation site. A coding sequence of an expression vector is operatively linked to a transcription terminating region. To bring a coding sequence under control of a promoter, it is necessary to position the translation initiation site of the translational reading frame of the peptide or polypeptide between one and about fifty nucleotides downstream (3') of the promoter. Examples of particular promoters are provided infra. Expression vectors and methods for their construction are known to those familiar with the art.

Suitable vectors include plasmids, and viral vectors such as herpes viruses, retroviruses, vaccinia viruses, attenuated vaccinia viruses, canary pox viruses, adenoviruses and adeno-associated viruses, among others.

The application of antigen-encoding genes to the mucosal induction of CTL in humans can utilize either in vivo or ex vivo based approaches.

The ex vivo method includes the steps of harvesting cells (e.g., dendritic cells) from a subject, culturing the cells, transducing them with an expression vector, and maintaining the cells under conditions suitable for expression of the soluble antigen. These methods are well known in the art of molecular biology. The transduction step is accomplished by any standard means used for ex vivo gene therapy, including calcium phosphate, lipofection, electroporation, viral infection, and biolistic gene transfer. Cells that have been successfully transduced are then selected, for example, for expression of a drug resistance gene. The cells can then be lethally irradiated (if desired) and injected or implanted into the subject. IL-12 and IFNγ can be administered either systemically or to the relevant mucosal surface as discussed above (Section B.2.1).

The in vivo approach requires delivery of a genetic construct directly into the mucosa of a subject, preferably targeting it to the cells or tissue of interest (e.g., dendritic cells in PP). This can be achieved by administering it directly to the relevant mucosa (e.g., IR in the case of PP). Tissue specific targeting can also be achieved by the use of a molecular conjugate composed of a plasmid or other vector attached to poly-L-lysine by electrostatic or covalent forces. Poly-L-lysine binds to a ligand that can bind to a receptor on target cells (Cristiano et al. *J. Mol. Med* 73:479 (1995)). Similarly, cell specific antibodies of the type described supra in Section B.2.1 can be bound to vectors and thereby target them to the relevant cells of the mucosal immune system. A promoter inducing relatively tissue or cell-specific expression can be used to achieve a further level of targeting. Appropriate tissue-specific promoters include, for example, the inducible IL-2 (Thompson et al., *Mol. Cell. Diol.* 12: 1043 (1992)), IL-4 (Todd et al., *J. Exp. Med.* 177:1663 (1993)) and IFNγ (Penix et al., *J. Exp. Med.* 178:483 (1993)) T-cell targeting promoters. These promoters would allow production of the soluble antigens in lymphoid tissue, including mucosal lymphoid tissue, e.g., PP. Naturally, an ideal promoter would be a dendritic cell specific promoter.

Vectors can also be delivered by incorporation into liposomes or other delivery vehicles either alone or co-incorporated with cell specific antibodies, as described supra in Section B.2.1.

DNA or transfected cells can be administered in a pharmaceutically acceptable carrier. Pharmaceutically acceptable carriers are biologically compatible vehicles which are suitable for administration to a human, e.g., physiological saline. A therapeutically effective amount is an amount of the DNA of the invention which is capable of producing a medically desirable result in a treated animal. As is well known in the medical arts, the dosage for any one patient depends upon many factors, including the patient's size, body surface area, age, the particular compound to be administered, sex, time and route of administration, general health, and other drugs being administered concurrently. Dosages will vary, but a preferred dosage for administration of DNA is from approximately $10^6$ to $10^{12}$ copies of the DNA molecule. This dose can be repeatedly administered, as needed. Routes of administration will be the mucosal routes recited for soluble antigens supra in Section B.2.1. The mucosal adjuvants, IL-12 and IFNγ can also be administered in the same combinations, by the same routes and at the same dosages recited in Section B.2.1.

B.3 Sources of Peptides and Polypeptide

Peptides and polypeptides used in the methods of the invention can be obtained by a variety of means. Smaller peptides (less than 100 amino acids long) can be conveniently synthesized by standard chemical methods familiar to those skilled in the art (e.g, see Creighton, Proteins: Structures and Molecular Principles, W.H. Freeman and Co., N.Y. (1983)). Larger peptides (longer than 100 amino acids) can be produced by a number of methods including recombinant DNA technology (see infra). Some polypeptides (e.g., HIV-1, gp160, CT, LT, IL-12, or IFNγ) can be purchased from commercial sources.

Polypeptides such as HIV-1, gp160, CT, IL-12, or IFNγ, can be purified from biological sources by methods well-known to those skilled in the art (Protein Purification, Principles and Practice, second edition (1987) Scopes, Springer Verlag, N.Y.). They can also be produced in their naturally occurring, truncated, chimeric (as in the CLUVAC, for example), or fusion protein forms by recombinant DNA technology using techniques well known in the art. These methods include, for example, in vitro recombinant DNA techniques, synthetic techniques, and in vivo genetic recombination. See, for example, the techniques described in Sambrook et al. (1989) Molecular Cloning, A Laboratory Manual, Cold Spring Harbor Press, N.Y.,; and Ausubel et al., eds. (1989), Current Protocols in Molecular Biology, Green Publishing Associates, Inc., and John Wiley & Sons, Inc., N.Y. Alternatively, RNA encoding the proteins can be chemically synthesized. See, for example, the techniques described in Oligonucleotide Synthesis, (1984) Gait, M. J. ed., IRL Press, Oxford, which is incorporated by reference herein in its entirety.

A variety of host-expression vector systems can be utilized to express the nucleotide sequences. Where the peptide or polypeptide is soluble, it can be recovered from: (a) the culture, i.e., from the host cell in cases where the peptide or polypeptide is not secreted; or (b) from the culture medium in cases where the peptide or polypeptide is secreted by the cells, The expression systems also encompass engineered host cells that express the polypeptide in situ, i.e., anchored in the cell membrane. Purification or enrichment of the polypeptide from such an expression system can be accomplished using appropriate detergents and lipid micelles and methods well known to those skilled in the art. Alternatively, such engineered host cells themselves can be used in situations where it is important not only to retain the structural and functional characteristics of the protein, but also to assess biological activity.

The expression systems that can be used for purposes of the invention include but are not limited to microorganisms such as bacteria (for example, *E. coli* and *B. subtilis*) transformed with recombinant bacteriophage DNA, plasmid DNA or cosmid DNA expression vectors containing the nucleotide sequences; yeast transformed with recombinant yeast expression vectors; insect cells infected with recombinant viral expression vectors (baculovirus); plant cell systems infected with recombinant viral expression vectors (e.g., cauliflower mosaic virus, CAMV; tobacco mosaic virus, TMV) or transformed with recombinant plasmid expression vectors; or mammalian cells (e.g., COS, CHO, BHK, 293, 3T3) harboring recombinant expression constructs containing promoters derived from the genome of mammalian cells (e.g., metallothionein promoter) or from mammalian viruses.

In bacterial systems, a number of expression vectors can be advantageously selected depending upon the use intended for the gene product being expressed. For example, when a large quantity of such a protein is to be produced, e.g., for in vivo immunization, vectors which direct the expression of high levels of fusion protein products that are readily purified can be desirable. Such vectors include, but are not limited to, the *E. coli* expression vector pUR278, (Ruther et al., *EMBO J*. 2:1791 (1983)), in which the coding sequence can be ligated individually into the vector in frame with the lacZ coding region so that a fusion protein is produced; pIN vectors (Inouye & Inouye, *Nucleic Acids Res*. 1:3101 (1985); Van Heeke & Schuster, *J. Biol. Chem*. 264:5503 (1989)); and the like. PGEX vectors can also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The PGEX vectors are designed to include thrombin or factor Xa protease cleavage sites so that the cloned target gene product can be released from the GST moiety.

In mammalian host cells, a number of viral-based expression systems can be utilized. In cases where an adenovirus is used as an expression vector, the nucleotide sequence of interest can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) will result in a recombinant virus that is viable and capable of expressing the gene product in infected hosts (e.g., See Logan and Shenk, *Proc. Natl. Acad. Sci. USA* 81:3655 (1984)). Specific initiation signals can also be required for efficient translation of inserted nucleotide sequences. These signals include the ATG initiation codon and adjacent sequences. In cases where an entire gene or cDNA, including its own initiation codon and adjacent sequences, is inserted into the appropriate expression vector, no additional translational control signals may be needed. However, in cases where only a portion of the coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, etc. (Bittner et al., *Methods in Enzymol*. 153:516 (1987)).

In addition, a host cell strain can be chosen which modulates the expression of the inserted sequences, or modifies and processes the gene product in the specific fashion desired. Such modifications (e.g., glycosylation) and processing (e.g., cleavage) of protein products may be important for the function of the protein. Appropriate cell lines or host systems can be chosen to ensure the correct modification and processing of the foreign protein expressed. Mammalian host cells include but are not limited to CHO, VERO, BHK, HeLa, COS, MDCK, 293, 3T3, and WI38.

For long-term, high-yield production of recombinant proteins, stable expression is preferred. For example, cell lines which stably express the sequences described above can be engineered. Rather than using expression vectors which contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells can be allowed to grow for 1–2 days in an enriched medium, and then are switched to a selective medium. The selectable marker in the recombinant plasmid confers resistance to the selection and allows cells to stably integrate the plasmid into their chromosomes and grow to form foci which in turn can be cloned and expanded into cell lines. This method can advantageously be used to engineer cell lines which express the gene product. Such engineered cell lines can be particularly useful in screening and evaluation of compounds that affect the endogenous activity of the gene product.

A fusion protein can be readily purified by autilizing an antibody or a ligand that specifically binds to the fusion protein being expressed. For example, a system described by Janknecht et al., *Proc. Natl. Acad. Sci. USA* 88:8972 (1991) allows for the ready purification of non-denatured fusion proteins expressed in human cell lines. In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni_{2+}$ nitriloacetic acid-agarose columns and histidine-tagged proteins are selectively eluted with imidazole-containing buffers. If desired, the histidine tag can be selectively cleaved with an appropriate enzyme.

The following examples are meant to illustrate the invention and not to limit it.

EXAMPLES

Materials and Methods

Human IR immunization Soluble antigens of the invention are dissolved in a pharmaceutically acceptable carrier, e.g., physiological saline and administered with and without adjuvant and with or without cytokines, e.g., IL-12 and/or IFNγ. The latter can be administered systemically or together with the antigen. Dosages of soluble antigen are approximately 0.001 mg to 100 mg per administration. Administration can be single, or multiple. In the case of multiple immunizations, there can, for example, be four weekly administrations, followed (if desired) by a booster administration several months (e.g., two, three, four, six, eight or twelve) or several years (e.g., two, three, four, five, ten, twenty or thirty) thereafter. Administration of the antigen (with and without adjuvant and with and without cytokine) can be by IR insertion of a suppository into which the immunizing composition has been incorporated, by enema or by flexible sigmoidoscope.

CTL activation cultures At various time points after immunization (different for each experiment), CTL activity was assessed. BALB/c mice were sacrificed and the intestines and SP were surgically removed. Single cell suspensions were prepared from the organs by methods familiar to those of average skill in the art. In the case of PP and LP, the PP were first dissected from the outer surface of the intestine. The rest of the intestine was cut into small fragments 1 to 3 mm square which were suspended in phosphate buffered saline (PBS). The tissue fragment suspension was stirred for 20 minutes at room temperature and shaken under the same conditions to liberate the intraepithelial lymphocytes (IEL) from the tissue. The suspended IEL were discarded and tissue fragments were treated with collagenase type VIII (Sigma) (300 U/ml) dissolved in PBS for 1 hour at room temperature to release the LP cells. PP cells were extracted from the dissected PP by the same collagenase treatment. Cells (PP or LP) were then placed on a discontinuous gradient containing 75% and 40% of Percoll, followed by centrifugation at 2,000 r.p.m. for 20 minutes. Lymphocytes were harvested from the 75%/40% interface and washed two times. Immune cells from SP, PP, LP were cultured with 1 $\mu$M P18IIIB-I10 peptide at $5\times10^6$ per/milliliter in 24-well culture plates in complete T cell medium (CTM): RPMI 1640 containing 10% fetal bovine serum, 2 mM L-glutamine, penicillin (100 U/ml), streptomycin (100 $\mu$g/ml), and $5\times10^{-5}$ M 2-mercaptoethanol. P18IIIB-I10 is a peptide containing the minimal essential CTL epitope of P18IIIB (SEQ ID NO:15) and has the sequence: RGPGRAFVTI (SEQ ID NO:16). Three days later, 10% supernatant from concanavalin A activated spleen cells was added as a source of interleukin-2 (IL-2). After 7 days of culture, LP lymphocytes (LPL) were stimulated in a second 7 day culture with 1 $\mu$M P18IIIB-I10 peptide (SEQ ID NO:16) together with $4\times10^6$ of 3300-rad irradiated syngeneic SP cells. Immune SP and PP cells were similarly stimulated in vitro for two 7-day culture periods before assay. Cytolytic activity of CTL was measured by a 4-hour assay with $^{51}$Cr labeled P815 targets using a method familiar to those of ordinary skill in the art. For testing the peptide specificity of CTL, $^{51}$Cr-labeled P815 targets were pulsed for 2 hours with peptide at the beginning of the assay. The percent specific $^{51}$Cr release was calculated as 100× (experimental release-spontaneous release)/(maximum release-spontaneous release). Maximum release was determined from supernatants of cells that were lysed by addition of 5% Triton-X 100. As a control, spontaneous release was determined from target cells incubated without added effector cells. Standard errors of the mean of triplicate cultures were all <5% of the mean.

Viral Plague assay Six days after IR challenge with recombinant vaccinia virus expressing HIV-1 IIIB gp160 (vPE16), mice were sacrificed. Their ovaries were removed, dissociated into single cell suspensions and assayed for vPE16 titer by plating serial 10-fold dilutions on a plate of BSC-2 indicator cells, staining with crystal violet and counting plaques at each dilution. The minimal detectable level of virus was 70 plaque forming units (pfu).

Example 1

Comparison of Mucosal and Systemic CTL Responses After Mucosal and Systemic Immunization Mice were immunized IR with 4 doses (on days 0, 7, 14 and 21) of the HIV-1 CLUVAC PCLUS3-18IIIB (SEQ ID NO:2) (50 $\mu$g/mouse). 5 weeks to 6 months after the first dose, antigen-specific T cells were isolated from PP, LP and SP and tested for the presence of HIV-1 P18IIIB peptide specific CTL (FIG. 1), as described above. Closed squares show killing of P18IIIB-I10 (SEQ ID NO:16)-pulsed targets and open diamonds show killing on unpulsed targets. IR immunization induced long-lasting protective immune responses: antigen-specific CTL were detected in mucosal inductive (PP) and effector (LP) sites and in a systemic site (SP) at least 6 months after immunization. In contrast, systemic immunization (s.c. in incomplete Freund's adjuvant) induced CTL in the spleen but not in the mucosal immune system (i.e., PP and LP).

Example 2

Comparison of CTL Responses with and without a Mucosal Adjuvant

Figure 2:
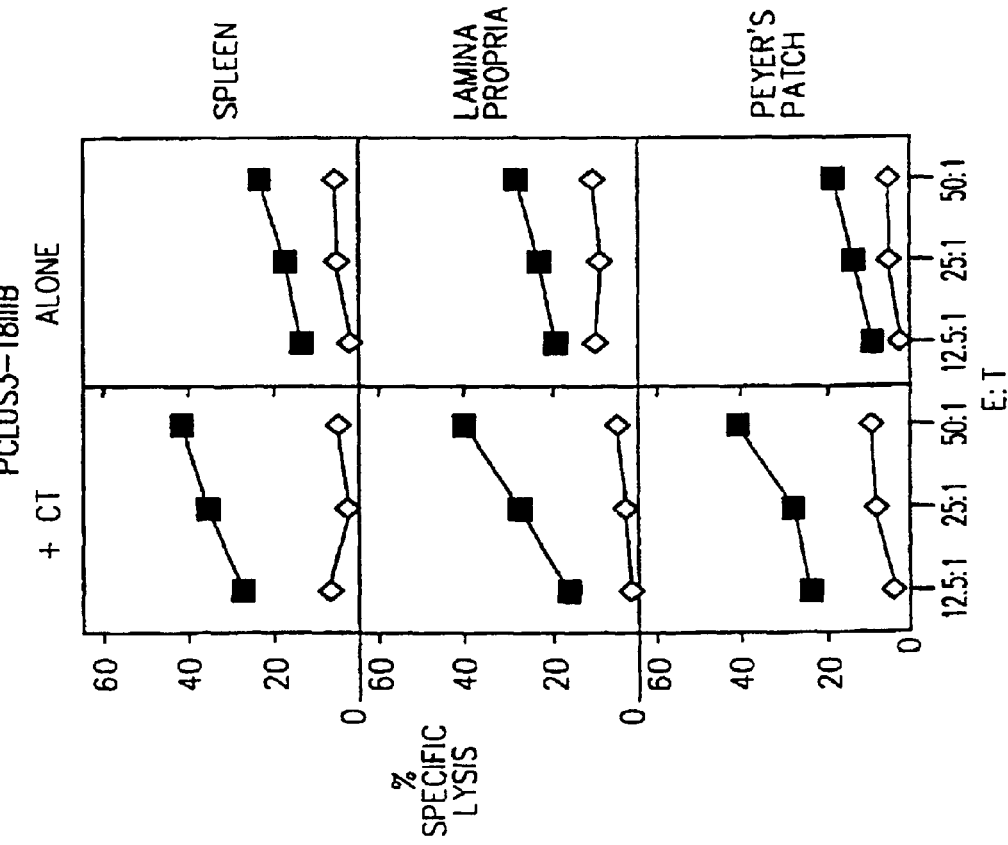
FIG. 2 is a series of line graphs showing the results of a CTL assay. CT enhanced (but was not essential) for induction of CTL by IR administration of antigenic peptide.

BALB/c mice were immunized IR with 4 doses of the synthetic HIV-1 CLUVAC PCLUS3-18IIIB (SEQ ID NO:2) (50 $\mu$g/mouse per immunization) alone, i.e., in the absence of adjuvant or cytokine on days 0, 7, 14 and 21. In parallel, another group of mice was immunized IR with PCLUS3-P18IIIB (SEQ ID NO:2) HIV-1 peptide in combination with CT (1eg/mouse). On day 35 antigen-specific T cells were isolated from PP, LP and SP. Immune cells from SP, PP, or LP were cultured and tested for antigen specific CTL (FIG. 2), as described above. Closed squares show killing of P18IIIB-I10 (SEQ ID NO:16) pulsed targets, and open diamonds show killing of unpulsed targets. IR administration of peptide alone induced a significant response. The response was enhanced by the co-administration of CT.

Example 3

Figure 3:
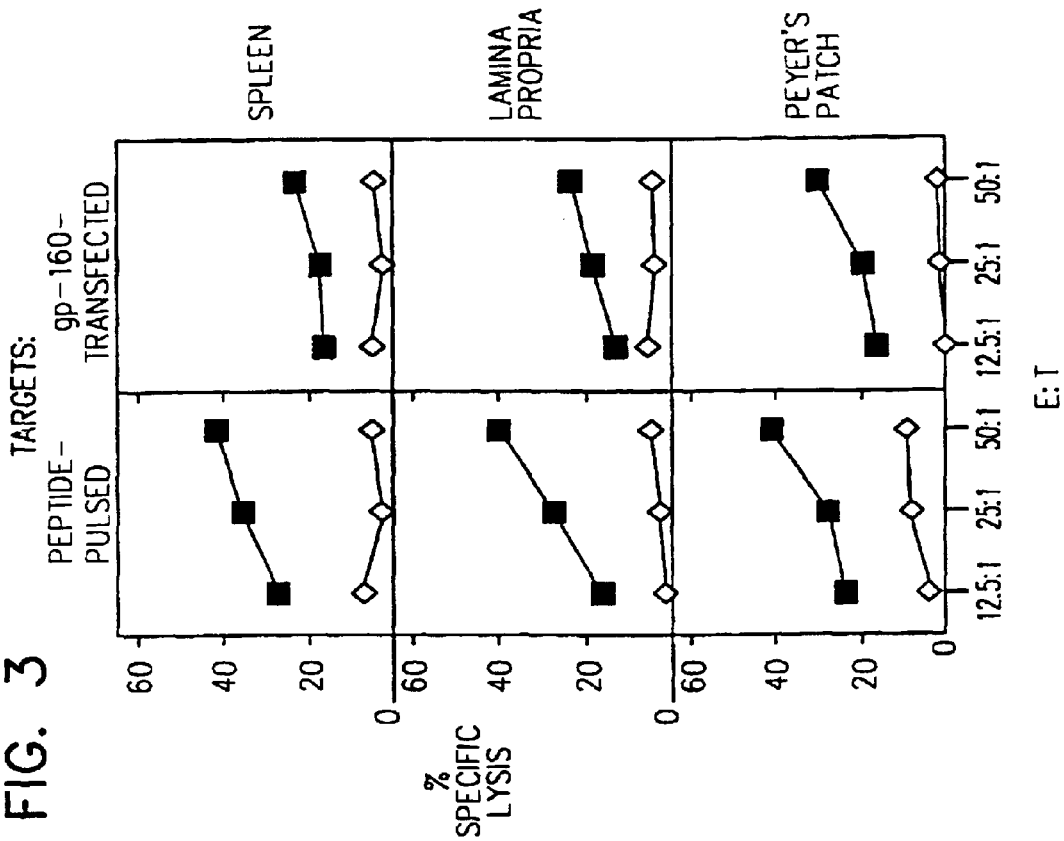
FIG. 3 is a series of line graphs showing the results of a CTL assay. CTL induced by IR immunization with an HIV-1 gp160 peptide specifically lysed target cells transfected with and expressing an HIV-1 gp160 gene.

CTL Induced by Mucosal Immunization Lyse Targets Expressing HRV-1 gp160 Envelope Protein Mice were immunized IR with 4 doses (on days 0, 7, 14 and 21) of the HIV-1 CLUVAC PCLUS3-18IIIB (SEQ ID NO:2) (5 $\mu$g/mouse per immunization) in the presence of CT (1 $\mu$g/mouse), on day 35, antigen-specific T cells were isolated from PP, LP and SP. Immune cells from SP, PP, or LP were cultured as described above. Cytolytic activity of CTL was measured using a standard $^{51}$Cr release assay (FIG. 3).

Three different cell lines were used as target cells: 15–12 cells, 3T3 18 Neo BALB/c cells and P815 cells. 15–12 cells are BALB/c 3T3 fibroblasts transfected with a vector encoding HIV-1 gp160 (Takahashi et al. *Proc. Natl. Acad. Sci. USA* 8:3105 (1988)); 3T3 18 Neo BALB/c cells are BALB/c 3T3 fibroblasts transfected with an expression vector containing a Neor gene but no gp160 gene; and P815 cells are untransfected cells that present antigenic peptides added to the culture. CTL lysis of gp160 expressing 15–12 cells (closed squares in right panels) was compared to that of control gp160 non-expressing 3T3 18 Neo BALB/c cells (open diamonds right panels). P815 target cells (left panel) were tested in the presence (closed squares) or absence (open diamonds) of P18IIIB-I10 peptide (SEQ ID NO:16) (1 $\mu$M). The percent specific 51Cr release was calculated as described above. CTL induced by IR immunization killed target cells either endogenously expressing HIV-gp160 or pulsed with P18IIIB peptide (SEQ ID NO:15).

Example 4

CTL Induced by IR Immunization are IL-12 Dependent

Figure 4:
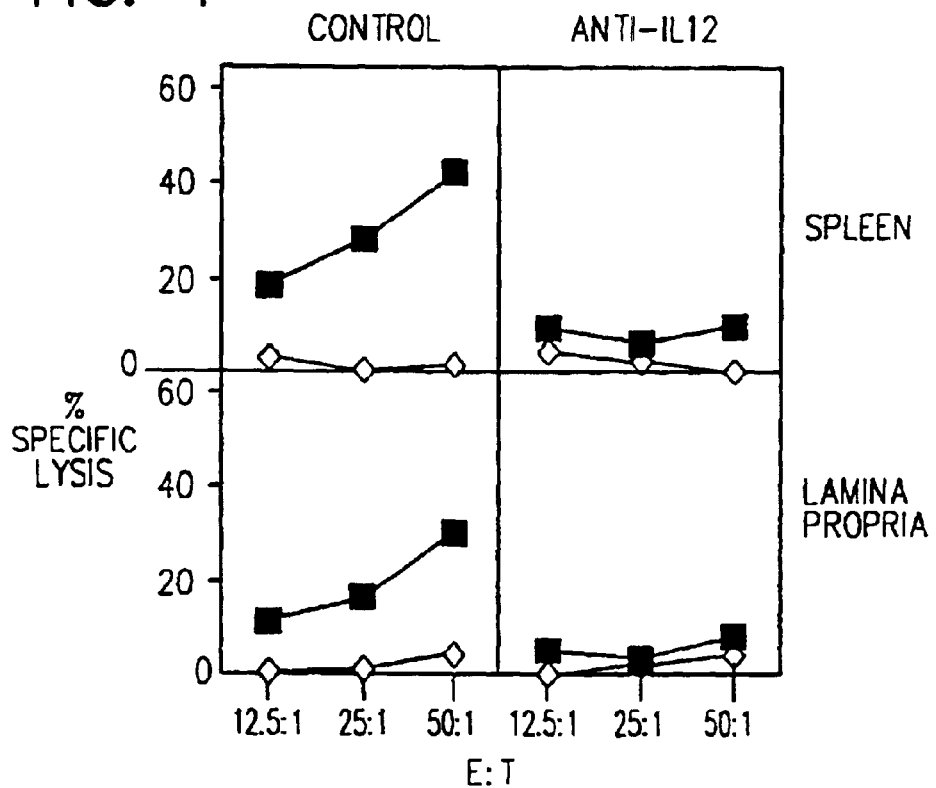
FIG. 4 is a series of line graphs showing the results of a CTL assay which indicated that IR induction of CTL was IL-12 dependent.

BALB/c mice were immunized IR with 4 doses (on days 0, 7, 14 and 21) of CLUVAC PCLUS3-18IIIB (SEQ ID NO:2) (50 μg/mouse per immunization) in combination with CT (1 μg/mouse). One day before and one day after immunization with peptide mice were treated intraperitoneally (i.p.) with anti-IL-12 antibody (0.5 mg/per injection: 4 mg/mouse total dose (FIG. 4, right panels) or were untreated (FIG. 4, left panels). On day 35, antigen-specific T cells were isolated from PP, LP and SP. Immune cells from SP, PP, or LP were cultured as described above. Cytolytic activity of CTL was measured (FIG. 4) as described above. For testing the peptide specificity of CTL, S51Cr labeled P815 targets were pulsed with peptide P18IIIB-I10 (SEQ ID NO:16) at the beginning of the assay (closed squares), or (as a control) left unpulsed i.e., without peptide (open diamonds). Induction of both mucosal and systemic CTL responses by IR immunization was IL-12-dependent, as shown by inhibition of induction of CTL in mice treated i.p. with anti-IL-12 antibody.

BALB/c mice were immunized IR on days 0, 7, 14 and 21 with either composition A containing the synthetic HIV-1 CLUVAC PCLUS3-18IIIB (SEQ ID NO:2) (50 μg/mouse per immunization), CT (10 μg/mouse per immunization), and recombinant IL-12 (1 μg/mouse per immunization), or composition B containing the synthetic HIV-1 CLUVAC PCLUS3-18IIIB (SEQ ID NO:2) (50 μg/mouse per immunization), and CT (10 μg/mouse per immunization), on day 35, antigen-specific T cells were isolated from PP and SP. Immune cells from PP (FIG. 9A) and SP (FIG. 9E) were separately cultured and tested for antigen specific CTL, as described above. FIG. 9A shows killing of peptide P18IIIB-I10 (SEQ ID NO:16) pulsed target cells by effector cells from mice immunized with composition A (i.e., antigen with IL-12) (open squares), and FIG. 9B shows killing is of the P18IIIB-I10 (SEQ ID NO:16) pulsed target cells by effector cells from mice immunized with composition B (i.e., antigen without IL-12) (open diamonds). In both FIGS. 9A and 9B, control data was obtained using the two effector populations tested on unpulsed targets. The enhanced CTL responses of both PP (FIG. 9A) and SP (FIG. 9B) effector cells from mice immunized IR with composition A compared to the responses elicited by IR immunization with composition B indicate that co-administration of IL-12 augments mucosal and systemic CTL responses. These data then provide independent evidence for the role of IL-12 in eliciting mucosal (and systemic) immunity by mucosal administration of antigens and confirm the findings of the antibody inhibition data described above.

Example 5

Intrarectal Peptide Immunization Protects Against Mucosal Challenge with EIV-gp160 Expressing Recombinant Vaccinia Virus

Figure 5:
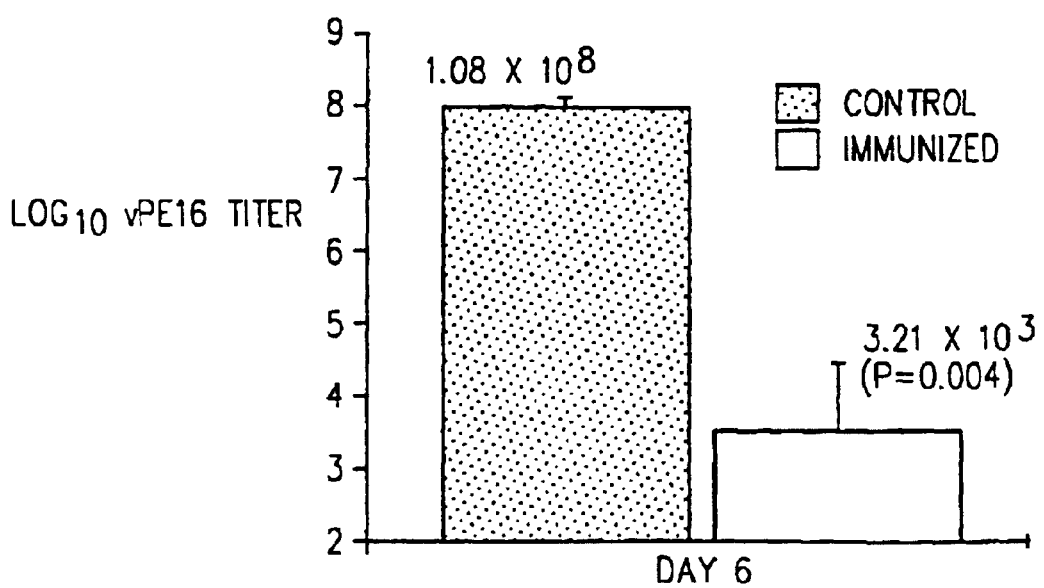
FIG. 5 is a bar graph showing that IR immunization protects against IR challenge with HIV-1 gp160 expressing recombinant vaccinia virus.

Groups of 5 mice were immunized IR with 4 doses of the HIV-1 CLUVAC PCLUS3-18IIIB (SEQ ID NO:2) (50 μg/mouse per immunization) on days 0, 7, 14 and 21 in combination with CT. On day 35, mice were challenged IR with $2.5 \times 10^7$ pfu of vaccinia virus expressing gp160 IIIB (vPE16). After 6 days, the mice were killed and their ovaries assayed for the presence of virus (FIG. 5) as described above. The left bar of FIG. 5 shows virus titer in the ovaries of unimmunized mice and the right bar shows virus titer in the ovaries of immunized mice. IR immunization with PLCUS3-18IIIB (SEQ ID NO:2) protected mice against IR challenge with vPE16 as shown by a 4.5-log reduction in viral pfu in ovaries compared to unimmunized animals (p<0.005).

Example 6

Comparison of Systemic CTL Responses Six Months After IR and IN Immunization

Mice were immunized IR or IN with 4 doses (on days 0, 7, 14 and 21) of the HIV-1 CLUVAC PCLUS3-18IIIB (SEQ ID NO:2) (50 μg/mouse). Six months after the first dose, antigen-specific T cells were isolated from SP and tested for the presence of HIV-1 P18IIIB-I10 (SEQ ID NO:16) peptide specific CTL (FIGS. 6A and 6B) as described above. Closed squares show killing of P18IIIB-I10 (SEQ ID NO:16)-pulsed targets and open diamonds show killing of unpulsed targets. The level of CTL activity induced by IR immunization (FIG. 6A) was higher than that induced by IN immunization (FIG. 6B). These data indicate that IR immunization induced potent, long-lasting, antigen-specific splenic immune responses.

Figure 7A:
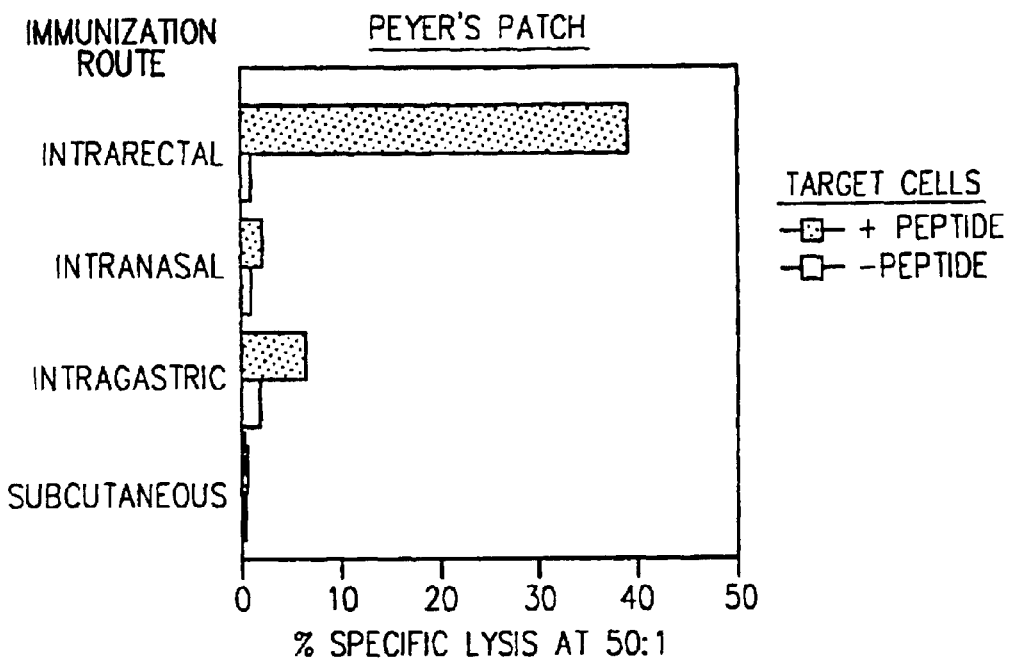
FIG. 7A is a bar graph showing the results of a CTL F assay using PP as effector cells.
Figure 7B:
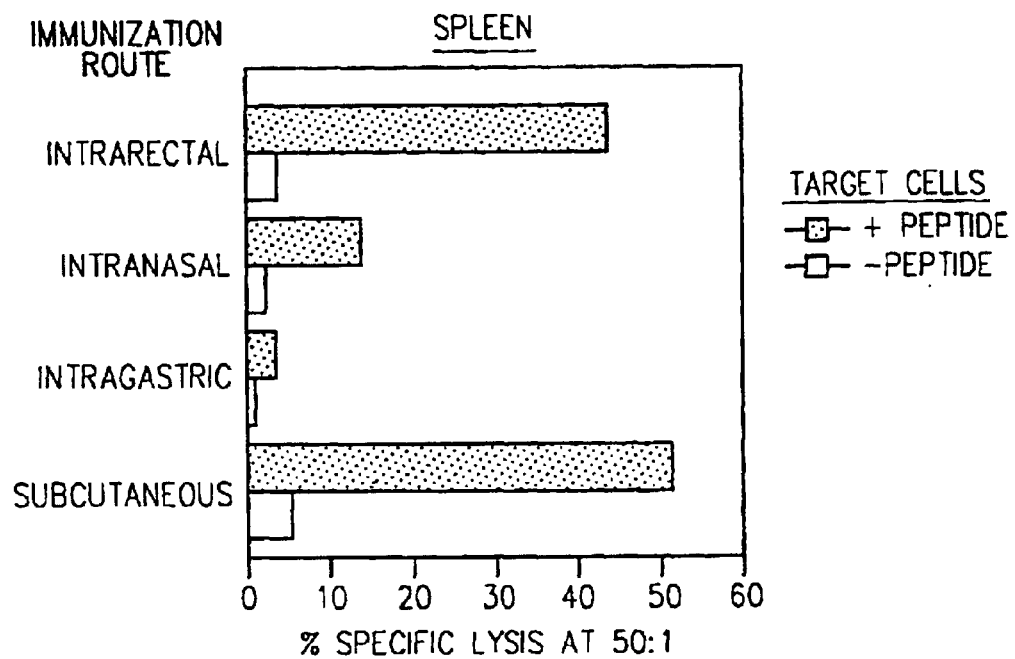
FIG. 7B is a bar graph showing the results of a CTL assay using SP cells as effector cells. PP and SP cells were obtained from animals thirty five days after mucosal (IR, IN, IG) or systemic (subcutaneous (SC)) immunization with an antigenic peptide.

To evaluate different routes of immunization, mice were immunized mucosally (IR, IN, IG) or systemically (SC) with 4 doses (on days 0, 7, 14 and 21) of the HIV-1 CLUVAC PCLUS3-18IIIB (SEQ ID NO:2) (50 μg/mouse). Thirty-five days after the first dose, antigen-specific T cells were isolated from PP and SP and tested for the presence of HIV-1 P18IIIB—I10 (SEQ ID NO:16) peptide-specific CTL as described above (FIG. 7). Closed bars show killing of P18IIIR-I10 (SEQ ID NO:16) pulsed targets and open bars show killing on unpulsed targets. The level of CTL activity induced by IR immunization was significantly higher in inductive mucosal tissue (PP) and much higher in systemic immunological tissue (SP) than that induced by the other mucosal routes (IN and IG). CTL activity was detected in both PP and SP after immunization via all three mucosal routes. Systemic immunization (SC) only resulted in significant CTL activity in SP.

Example 7

CTL Induced by IR Immunization are IFNγ Dependent

Wild-type BALB/c mice and BALB/c mice lacking the ability to produce functional IFNγ (IFNγ$^{-/-}$ mice) (Dalton et al., *Science* 259:1739 (1993); Tishon et al., *Virology* 212:244 (1995)) were immunized IR with 4 doses (on days 0, 7, 14 and 21) of CLUVAC PCLUS3-18IIIB (SEQ ID NO:2) (50 μg/mouse per immunization) in combination with CT (1 μg/mouse). On day 35, antigen-specific T cells were isolated from PP, LP and SP. Immune cells from SP, PP, or LP of wild type BALB/c and IFNγ$^{-/-}$ mice were cultured as described above. Cytolytic activity of. CTL was measured (FIG. 8A and FIG. 8B) as described above. The peptide specificity of CTL was tested as follows: $^{51}$Cr labeled P815 targets were pulsed with peptide P18IIIB-I10 (SEQ ID NO:16) at the beginning of the assay (solid bars), or (as a control) left unpulsed i.e., without peptide (open bars). Induction of both mucosal and systemic CTL responses by IR immunization was IFNγ dependent, as shown by the lack of detectable CTL activity in SP, PP, and LP cells from IFNγ$^{-/-}$ mice (FIG. 8B) and potent CTL activity in SP, PP, and LP cells from wild-type BALB/c mice (FIG. 8A).

Summarizing the foregoing results, mucosal, administration of an antigenic peptide to mice results in the induction of a protective CTL response detectable in both the inductive (Peyer's patch (PP)) and effector (lamina propria (LP)) sites of the intestinal mucosal immune system, as well as in systemic lymphoid tissue, i.e., spleen (SP). The mucosal CTL response is enhanced by co-administering the mucosal adjuvant, cholera toxin (CT) with the antigenic peptide, is inhibited by antibody that specifically binds to (thereby neutralizing the activity of) interleukin-12 (IL-12), and is not detectable in mice lacking the ability to produce functional interferon-γ (IFNγ). Furthermore, including IL-12 in the composition of antigenic peptide and CT used for IR immunization resulted in enhanced PP and SP CTL responses relative to those obtained by IR immunization with antigenic peptide, CT and no IL-12. IR immunization with the viral peptide resulted in protection from viral infection upon subsequent IR challenge with the appropriate virus.

Example 8

Comparison of Different HIV Vaccine Peptides for use in Eliciting Viral Mucosal Protection Because of the variability of the V3 loop of HIV, further studies were conducted comparing two cluster peptide constructs using the V3 loop and incorporating the CTL epitope P18 from strain IIIB (Ratner et al., Nature 313:277–284, (1985)) or MN (Gurgo et al., Virology 164:531–536, (1998)) of HIV-1. These studies were conducted as an exemplary analysis to demonstrate that HIV vaccine cluster peptide constructs can be prepared from different HIV strains and screened in side-by-side assays to optimize induction of mucosal CTL immunity.

Animals For each of the following Examples, female BALB/c mice were purchased from Frederick Cancer Research Center (Frederick, Md.). IFNγ$^{-/-}$ mice were purchased from Jackson Laboratories (Bar Harbor, Me.). Mice used in this study were 6–12 weeks old. The IFNγ$^{-/-}$ mice were maintained in a specific pathogen-free microisolator environment.

Immunization Mice were immunized with 4 doses of the synthetic HIV peptide vaccine construct PCLUS3-18IIIB (Ahlers et al., J. Immunol. 150:5647–5665, (1993)) (50 μg/mouse for each immunization) on days 0, 7, 14 and 21 in combination with cholera toxin (CT) (10 μg/lmouse) (List Biological Laboratories, Campbell, Calif.) by intrar tal administration. For subcutaneous imnmunization, incomplete Freund's adjuvant was used. rm IL-12 (a generous gift of Genetics Institute, Inc., Cambridge, Mass.) was delivered either intraperitoneally (IP) (1 μg) or intrarectally (1 μg) mixed with DOTAP (Boehringer Mannheim), a cationic lipofection agent, along with the peptide vaccine.

Cell purification Five weeks to 6 months after the first dose, antigen-specific T cells were isolated from Peyer's patches (PP), lamina propria (LP) and the spleen (SP). The Peyer's patches were carefully excised from the intestinal wall and dissociated into single cells by use of collagenase type VIII, 300 U/ml (Sigma) as described, Mega et al., Int. Immunol. 3:793–805, (1991). Our data showed that most PP CD3$^+$ T cells isolated from normal mice were CD4$^+$, while CD3$^+$CD8$^+$ T cells were less frequent. Further, collagenase did not alter expression of CD3, CD4, or CD8 on splenic T cells treated with this enzyme. Lamina propria lymphocyte (LPL) isolation was performed as described, Mega et al., Int. Immunol. 3:793–805, (1991). The small intestines were dissected from individual mice and the mesenteric and connective tissues carefully removed. Fecal material was flushed from the lumen with un-supplemented medium (RPMI 1640). After the PP were identified and removed from the intestinal wall, the intestines were opened longitudinally, cut into short segments, and washed extensively in RPMI containing 2% fetal bovine serum (FBS). To remove the epithelial cell layer, tissues were placed into 100 ml of 1 mM EDTA and incubated twice (first for 40 min and then for 20 min) at 37° C. with stirring. After the EDTA treatment, tissues were washed in complete RPMI medium for 10 min at room temperature and then placed into 50 ml of RPMI containing 10% FCS and incubated for 15 min at 370 with stirring. The tissues and medium were transferred to a 50 ml tube and shaken vigorously for 15 seconds, and then the medium containing epithelial cells was removed. This mechanical removal of cells was repeated twice more, using fresh medium each time, in order to completely remove the epithelial cell layer. Histologic examination revealed that the structure of the villi and lamina propria were preserved. To isolate LPL, tissues were cut into small pieces and incubated in RPMI 1640 containing collagenase type VIII 300 U/ml (Sigma) for 50 min at 37° C. with stirring. Supernatants containing cells were collected, washed and then re-suspended in complete RPMI 1640. This collagenase dissociation procedure was repeated two times and the isolated cells pooled and washed again. Cells were passed through a cotton-glass wool column to remove dead cells and tissue debris and then layered onto a discontinuous gradient containing 75% and 40% Percoll (Pharmacia Fine Chemicals, Pharmacia Inc., Sweden). After centrifugation (4° C., 600 g, 20 min), the interface layer between the 75% and 40% Percoll was carefully removed and washed with incomplete medium. This procedure provided >90% viable lymphocytes with a cell yield of 1.5–2×10$^6$ lymphocytes/mouse. The SP were aseptically removed and single cell suspensions prepared by gently teasing them through sterile screens. The erythrocytes were lysed in Tris-buffered ammonium chloride and the remaining cells washed extensively in RPMI 1640 containing 20/o FBS.

Cytotoxic T lvmphocyte assay Immune cells from SP, PP, LP were cultured at 5×10$^6$ per/milliliter in 24-well culture plates in complete T cell medium (CTM): RPMI 1640 containing 10% FBS, 2 mM L-glutamine, penicillin (100 U/ml), streptomycin (100 μg/ml), and 5×10$^{-5}$ M 2-mercaptoethanol. Three days later we added 10% concanavalin A supernatant-containing medium as a source of IL-2. LPL were studied after 7 days stimulation with I$\mu$M P18IIIB-I10 peptide together with 4×10$^6$ of 3300-rad irradiated syngeneic spleen cells. SP and PP cells were stimulated in vitro similarly for one or two 7-day culture periods before assay. Cytolytic activity of CTL lines was measured by a 4-hour assay with $^{51}$Cr labeled targets. Two different cell lines were used as a target cells: 1) 15–12 cells, Takahashi et al., Proc. Natl. Acad. Sci. USA 85:3105–3109 (1988) (BALB/c 3T3 fibroblasts transfected with HIV-1IIIB gp160 and endogenously expressing HIV gp160), compared with 18 Neo BALB/c 3T3 fibroblasts transfected with NeO$^R$ alone as a control, and 2) P815 targets tested in the presence or absence of I10 peptide (I$\mu$M). For testing the peptide specificity of $^{51}$Cr labeled P815 targets were pulsed for 2 hours with peptide at the beginning of the assay. The percent specific $^{51}$Cr release was calculated as 100× (experimental release-spontaneous release)/(Maximum release-spontaneous release). Maximum release was determined from supernatants of cells that were lysed by addition of 5% Triton-X 100. Spontaneous release was determined from target cells incubated without added effector cells.

Vaccinia virus Recombinant vaccinia virus vPE16 expresses the HIV-1 gp160 gene from isolate IIIB (BH8) (Earl et al., J. Virol. 64:2448–2451 (1990)). Expression is directed by the compound early/late P7.5 promoter. Two copies of the sequence T5NT, which serves as a transcription termination signal for early vaccinia virus genes, are present in the IIIB gp 160 gene. Both of these have been altered in vPE16, so as to retain the original coding sequence and allow early transcription of the gene. The virus, vSC8, is used as a negative control without gp160 (Chakrabarti et al., Mol. Cell Biol. 5:3403–3409 (1985)). Both vPE16 and VSC8 express beta-galactosidase.

Determination of virus titer in the ovary On day 35 or 6 months after cluster peptide HIV vaccine immunization, mice were challenged intrarectally with $2.5 \times 10^7$ or $5 \times 10^7$ pfu of vaccinia virus expressing gp160 IIIB (vPE16). Six days after the challenge with recombinant vaccinia virus expressing HIV-gp160, the mice were killed and ovaries were removed, homogenized, sonicated, and assayed for vPE16 titer by plating serial 10-fold dilutions on a plate of BSC-2 indicator cells staining with crystal violet and counting plaques at each dilution. The minimal detectable level of virus was 100 pfu.

To compare different HIV vaccine cluster peptide constructs, BALB/c mice were immunized intrarectally with peptide (PCLUS3-18IIIB or PCLUS3-18MN) in the presence of CT as a mucosal adjuvant weekly for four weeks (on days 0, 7, 14, and 21). Mice were studied either two weeks later (day 35) or at six months for memory CTL responses in the Peyer's Patches (PP) or spleen (SP). IR immunization with both peptides PCLUS3-18IIIB or PCLUS3-18MN in combination with CT induces a P18-specific CTL response in the intestinal PP (FIG. 10, panel A) and in the spleen (FIG. 10, panel B).

However, the level of CTL response after IR immunization with PCLUS3-18MN was significantly lower than after IR immunization with PCLUS3-18IIIB. The difference may reflect a higher affinity of the minimal 10-mer P18IIIB-I10, compared to P18MN-T10, for $H\text{-}2D^d$ (Takahashi et al., Science 246:118–121 (1989); Takeshita et al., J. Immunol. 154:1973–1986 (1995)). Also, much higher production of IFNγ by mucosal P18IIIB-specific $CD8^+$ CTL was observed compared to P18-MN-specific CTL after stimulation with specific peptide in vitro for 48 hours. When tested on 15–12 gp160 IIIB-transfected fibroblast targets endogenously expressing gp 160IIB, the CTL elicited by immunization with PCLUS3-18IIIB also killed these targets. On the basis of these observations, the PCLUS3-18IIIB construct was used in the protection experiments described below.

Example 9

Mucosal Immunization of Mice with Cluster Peptide Construct Provides Longlasting Protection from Infection with Recombinant Vaccinia Virus Expressing HIVg160

In the foregoing Examples, the ability of the mucosal immune responses induced by the HIV cluster peptide vaccine to protect against virus challenge via a mucosal route is demonstrated. To determine the specificity of this protection for recombinant protein HIV-1 IIIB gp160, IR immunized mice were challenged on day 35 after the start of immunization by IR infusion with vaccinia virus expressing HIV-1 IIIB gp 160 (vPE16), or with control vaccinia virus expressing β-galactosidase (vSC8). Unimmunized animals challenged with vPE16 or vSCB served as controls. Six days after the challenge, mice were sacrificed and the ovaries were removed and assayed for vaccinia titer (6 days after infection with vaccinia, the ovaries contain the highest titer of virus).

Figure 11:
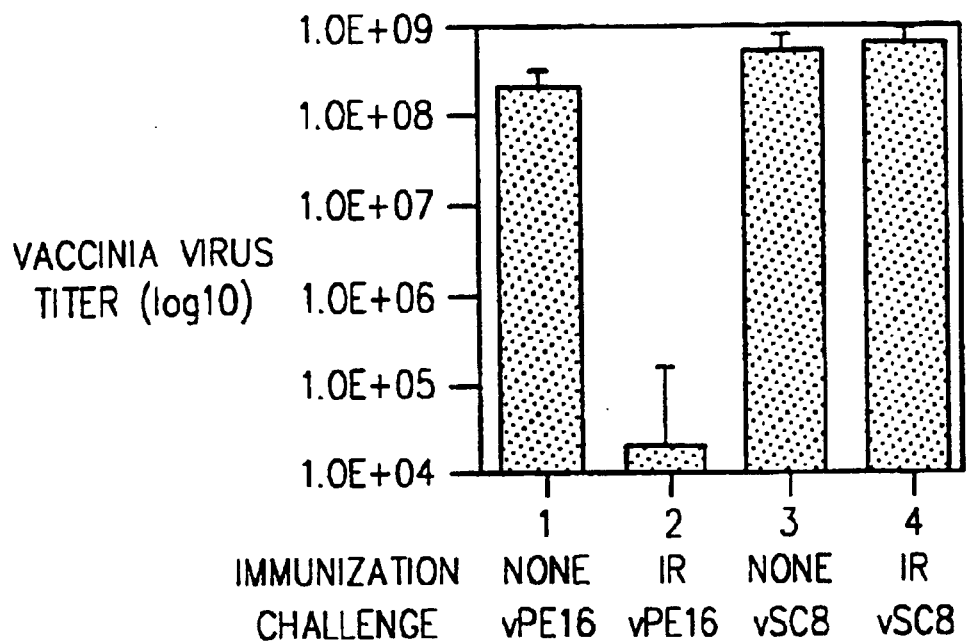
FIG. 11 demonstrates that protection induced by mucosal immunization with HIV-1 peptide vaccine is specific. On day 35, mice were challenged intra-rectally with 2.5×10$^7$ plaque-forming units (pfu) of vaccinia virus expressing gp 160IIIB (vPE16) or with 2.5×10$^7$ pfu of vaccinia virus expressing β-galactosidase (vSC8). Bars=SEM of five mice per group. The difference is significant at P<0.01 by Student's test.

IR immunization with the synthetic HIV peptide vaccine protected mice against an IR challenge with vaccinia virus expressing HIV-1 IIIB gp160 compared to unimmunized controls, but did not protect against IR challenge with vaccinia virus expressing only an unrelated protein, β-galactosidase (FIG. 11). Thus, the protection was specific for virus expressing HIV-1 gp160, and any nonspecific inflammatory response induced by the peptide infusion intrarectally was not sufficient to protect against viral challenge two weeks after the last dose of the immunization.

Figure 12:
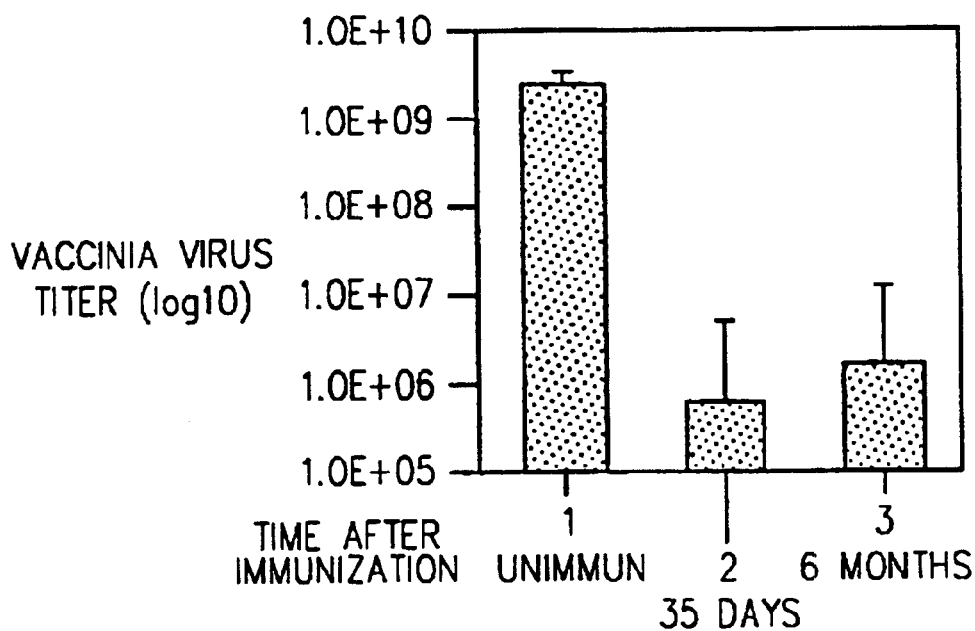
FIG. 12 demonstrates that protection induced by mucosal immunization with HIV-1 peptide vaccine is long-lasting. On day 35 or 6 months after the start of the immunization, mice were challenged intrarectally with 2.5×10$^7$ pfu of vaccinia virus expressing gp 160IIIB. Bars=SEM of five mice per group. The difference is significant at P<0.01 by Student's test.

Although the presence of mucosal memory CTL precursors was observed, requiring restimulation in vitro for activity 6 months after IR immunization (Belyakov et al., Proc. Nati. Acad. Sci. 95:1709–1714 (1998)), the strength and duration of protection remained unclear. To resolve this question, the IR immunized mice were challenged 6 months after the start of immunization with PCLUS3-18IIIB by IR administration with vaccinia virus expressing HIV-1 IIIB (vPE16). This study showed that, even 6 months after HIV cluster peptide immunization, BALB/c mice exhibit protection against recombinant HIV-vaccinia challenge (FIG. 12).

Example 10

Figure 13:
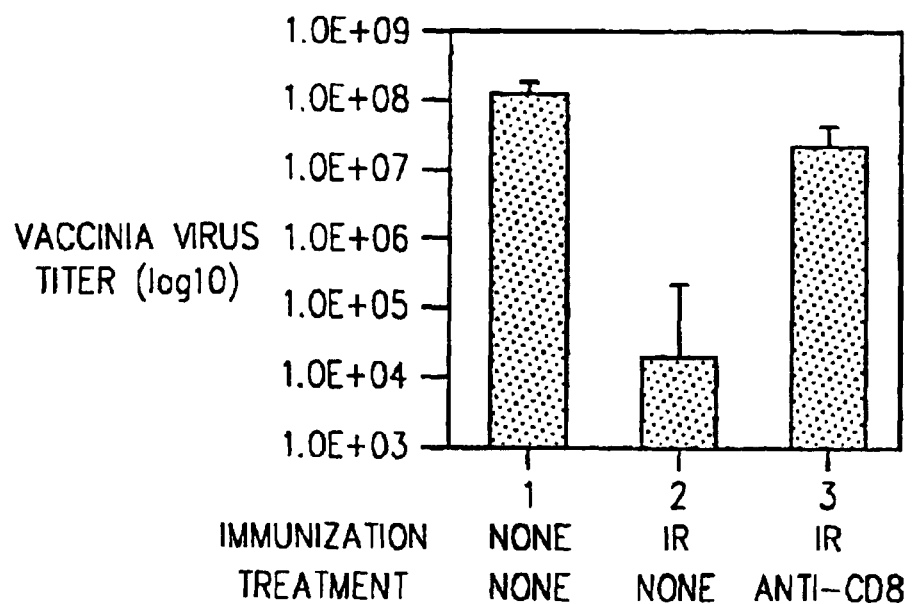
FIG. 13 demonstrates that protection induced by mucosal immunization with HIV-peptide is dependent on CD8 positive T-cells. BALB/c mice were treated IP with 0.5 mg monoclonal anti-CD8 antibody (clone 2.43, NIH Frederick, Md.) one day before and after each immunization and also two days before and three days after the challenge with vPE16. Mice were challenged intrarectally with 2×10$^7$ pfu of vPE16 vaccinia virus expressing gp 160IIIB.

Protection of Mice Against Mucosal Viral Challenge is Mediated by $CD8^+$ CTL in the Mucosal Site To determine the immune mechanism responsible for protection against mucosal challenge with virus expressing HIV gp160, mice were treated IP with 0.5 mg monoclonal anti-CD8 antibody (clone 2.43, NIH, Frederick, Md.) one day before and after each of the four immunizations and also two days before and three days after the challenge with vPE16. This treatment led to a significant inhibition of the protection against mucosal challenge with vPE16 (FIG. 13). Thus, protection in the mucosal site against the virus expressing HIV-1 gp160 is mediated by $CD8^+$ lymphocytes.

Figure 14A:
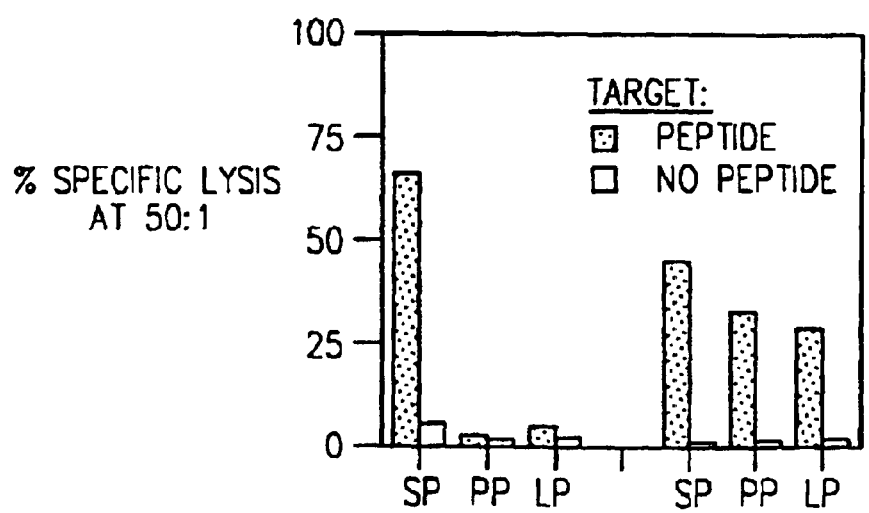
FIGS. 14A and 14B demonstrate that mucosal immunization with HIV-1 peptide induces mucosal CTL responses and stimulates protective immunity against intrarectal recombinant HIV-1 vaccinia challenge.

Because the HIV peptide constructs disclosed herein elicit both strong mucosal and systemic MHC class I restricted $CD8^+$ CTL responses (Belyakov et al., Proc. Nati. Acad. Sci. 95:1709–1714 (1998)), the role of these responses in mediating protection were further investigated. Because SC immunization with peptide vaccine elicits splenic but not mucosal CTL, whereas IR immunization elicits both (FIG. 14), SC and IR immunizations can be compared to determine whether systemic CTL are sufficient to protect against mucosal challenge, or whether local mucosal CTL are necessary. Accordingly, mice were immunized with PCLUS3-18IIIB plus IFA by the SC route or with PCLUS3-18IIIB and CT by the IR route on days 0, 7, 14 and 21, and compared these. On day 35 after the start of immunization, these groups of mice as well as unimmunized control mice were challenged by IR administration of vaccinia virus expressing HIV-1 gp160 (vPE16). Finally, six days after the challenge, mice were sacrificed and their ovaries assayed for viral titer.

Figure 14B:
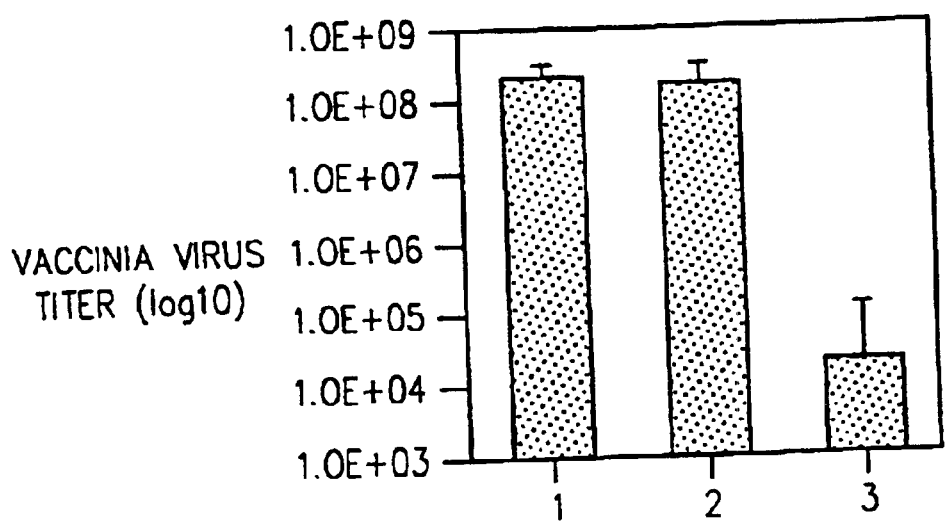

SC immunization with PCLUS3-18IIIB did not protect mice against mucosal challenge with vPE16, whereas IR immunization with the same peptide did protect (FIG. 14B). Thus, protection against mucosal challenge with virus expressing HIV-1 gp160 can be induced only by mucosal immunization of mice, and correlates with local mucosal CTL activity, not with splenic CTL activity. On this basis one can conclude that the $CD8^+$ CTL-mediated protection from mucosal challenge with recombinant vaccinia expressing HIV-1 gp160 requires local mucosal $CD8^+$ CTL, whereas a systemic CTL response is not sufficient.

Example 11

Figure 15A:
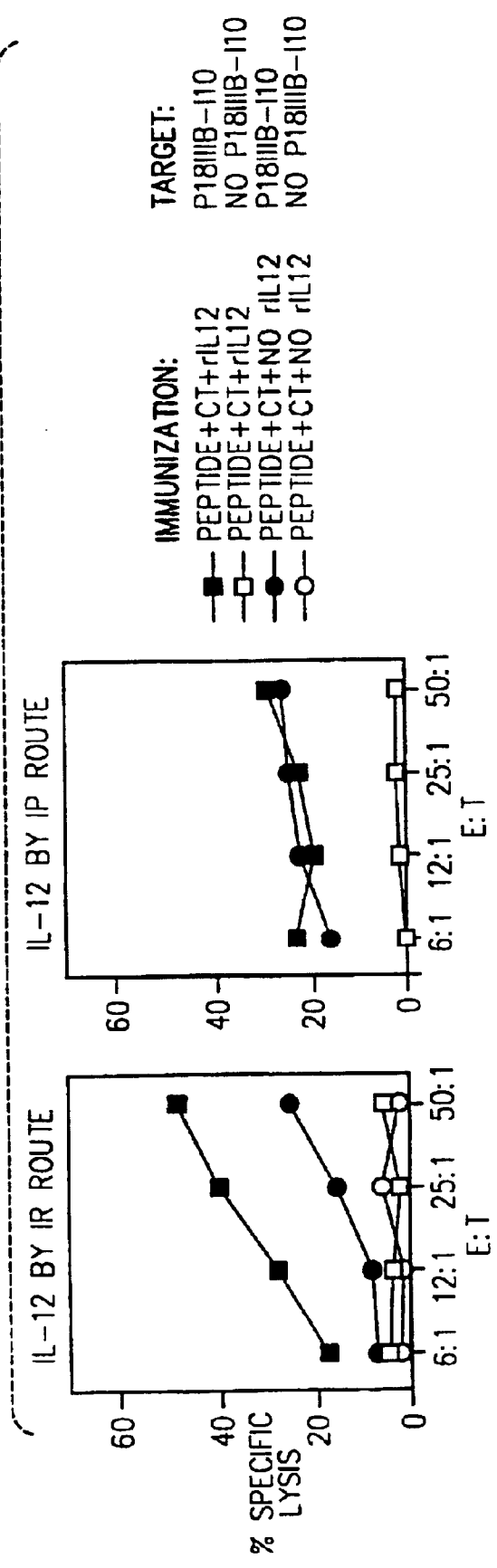
FIGS. 15A and 15B demonstrate enhancement of the mucosal (FIG. A) and systemic (FIG. B) CTL responses to HIV-1 peptide by the mucosal (not systemic) treatment with rmIL-12 BALB/C mice were treated by the IP route (right panels) or IR route (left panels) with 1 μg of the rmIL-12 each day of the IR immunization with PCLUS3-18IIIB (50 μg/mice). On day 35 HIV-specific Peyer's patch CTL (FIG. 15A) and spleen CTL (FIG. 15B) were studied.
Figure 15B:
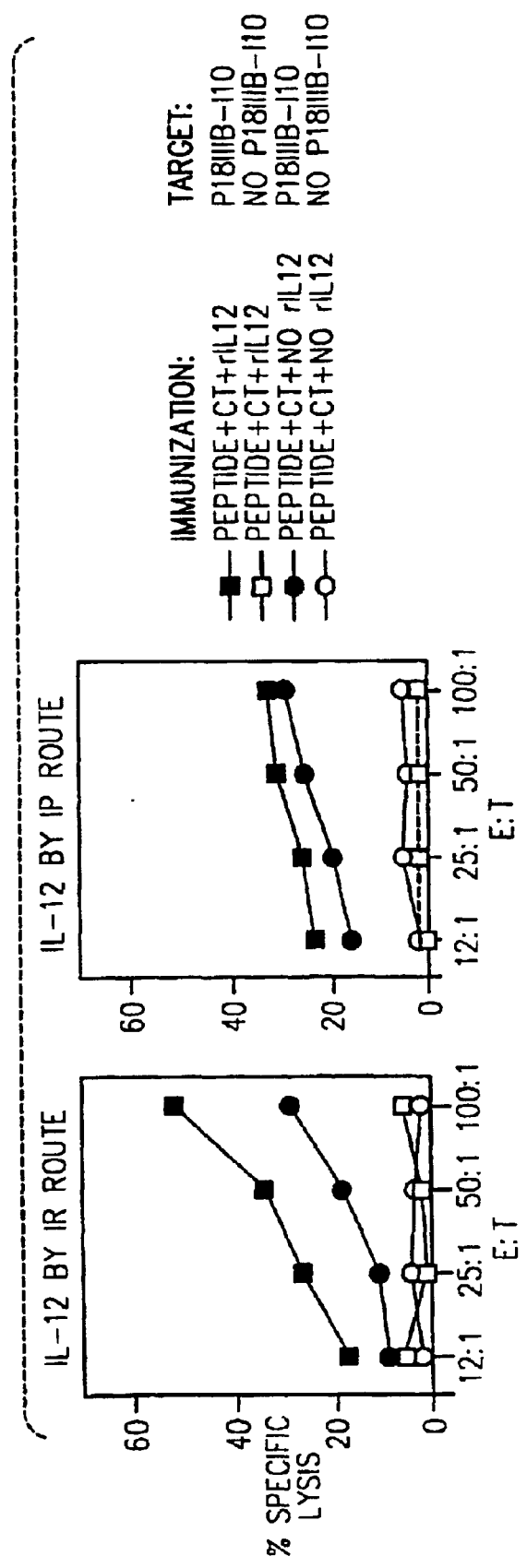

Cytokine Dependence and Enhancement of Protection by Local Administration of IL-12 with the Vaccine Induction of mucosal CTL by peptide vaccine is dependent on endogenous IL-12 in that it can be blocked by in vivo treatment of mice with anti-IL-12 (Belyakov et al.,

*Proc. Nati. Acad. Sci.* 95:1709–1714, (1998)). To further define the role of IL-12 in the CTL response and protection, BALB/c (H-2D$^d$) mice were treated by the IP route with 1 μg of the rmIL-12 each day of the IR immunization with PCLUS3-18IIIB (50 μg/mice). This treatment did not lead to significant changes in the HIV-specific CTL activity in either mucosal or systemic sites (FIG. 15). However, when the mice were treated with the rmIL-12 (1 μg)+DOTAP intrarectally together with peptide, we found a significant increase in the CTL level in both mucosal and systemic sites 35 days after the start of immunization (FIG. 15).

In view of the above results, the possibility that rmIL-12 administered at the local site and time of mucosal immunization might increase protection against mucosal challenge with vaccinia virus expressing HIV-1 gp160 was investigated. To address this question, BALB/c mice were immunized with the rmIL-12+DOTAP intrarectally together with peptide. The mice were then challenged mice on day 35 after the start of immunization by IR administration of vaccinia virus expressing HIV-1IIIB gp160. In this study, twice the dose of challenge virus was used, whereby the unimmunized mice had a titer of several times $10^{10}$ rather than several times $10^8$ seen in the previous Examples using a lower challenge dose. Nevertheless, the immunized mice showed a reduction of greater than 4 logs in virus titer, as had been seen in the earlier experiments (FIG. 16, bar 2).

Figure 16:
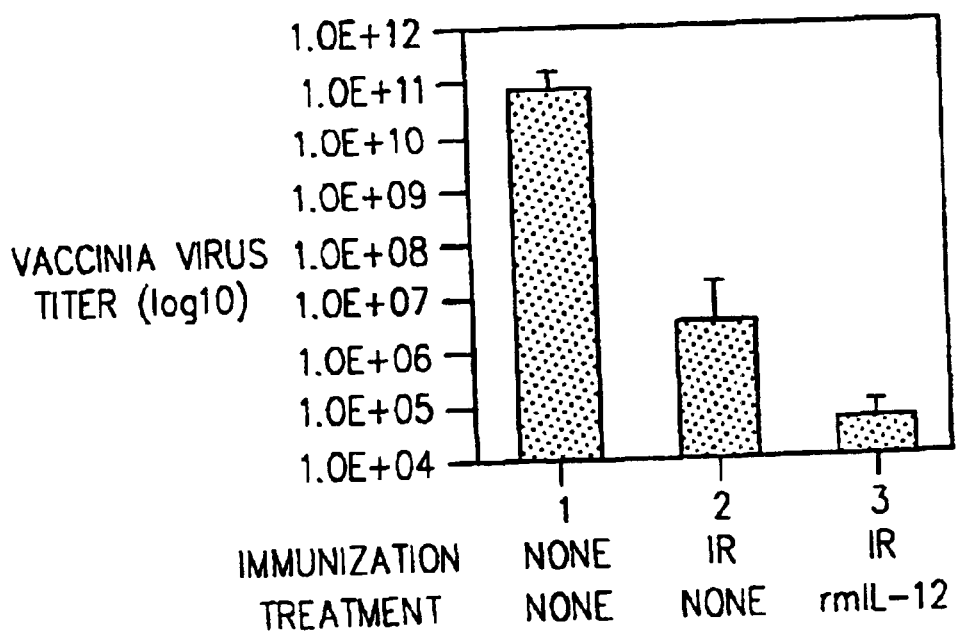
FIG. 16 demonstrates that mucosal treatment with rmIL-12 in DOTAP along with HIV peptide vaccine enhances protection against mucosal challenge with vaccinia virus expressing gp160IIIB (vPE16). Five mice per group were immunized IR on days 0, 7, 14 and 21 with no immunogen (bar 1), with 50 μg PCLUS3-18IIIB alone (bar 2), or with peptide plus 1 μg rmIL-12 in DOTAP (bar 3), and challenged on day 35 intrarectally with 5×10$^7$ pfu of vaccinia virus expressing gp 160IIIB. Viral pfu in the ovaries were determined six days later.

Importantly, IR immunization with the synthetic HIV peptide vaccine plus rmIL-12 protected mice against an IR challenge with this gp-160-recombinant vaccinia virus even more effectively than after the IR immunization with peptide alone (6-log reduction in viral pfu versus 4-log reduction, p<0.05) (FIG. 16, bar 3 versus bar 2).

Figure 17A:
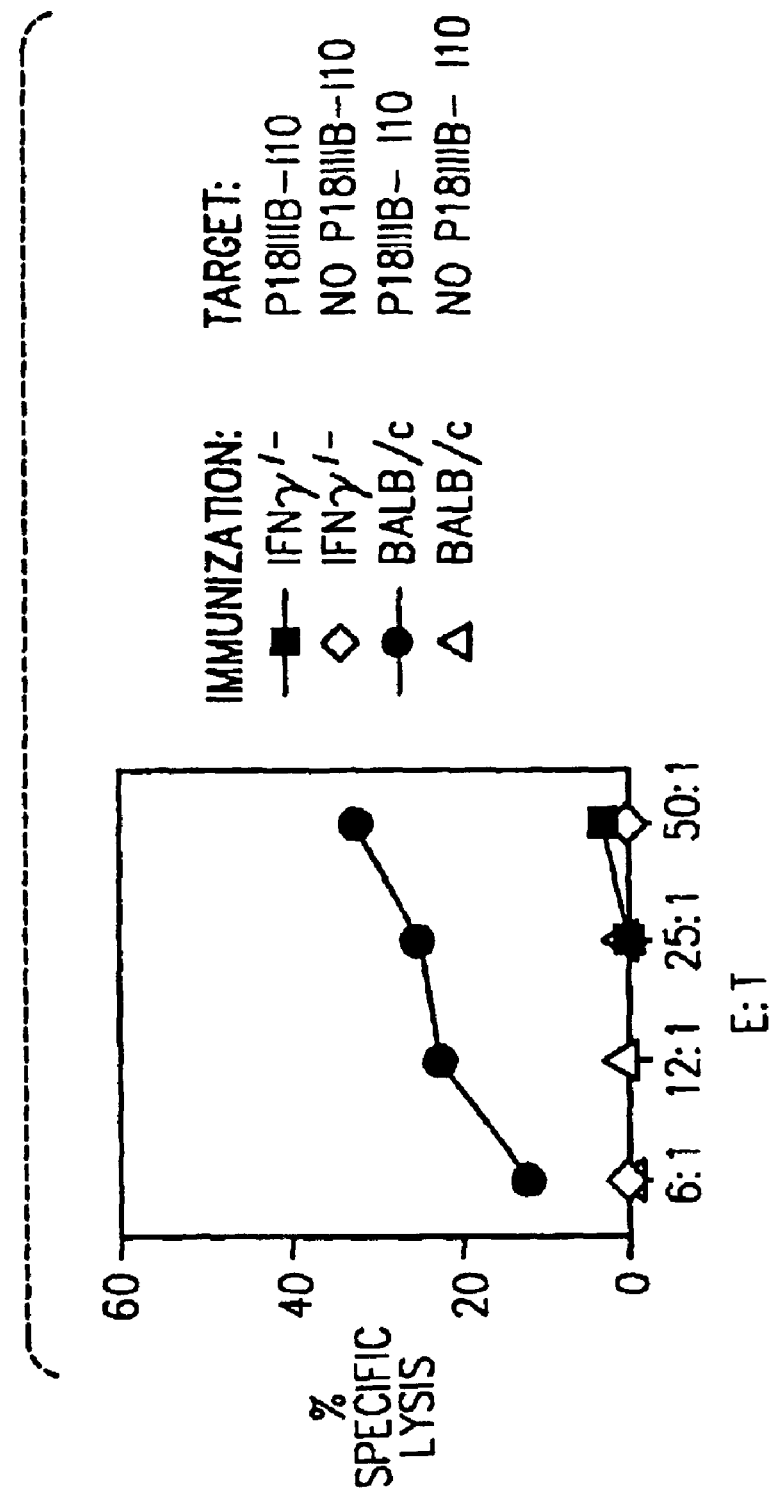

As the induction of mucosal CD8° CTL is strongly dependent on IL-12 and IFNγ (Belyakov et al., *Proc. Nati. Acad. Sci.* 95:1709–1714 (1998)), further studies were undertaken herein to determine which cytokine acts directly if, for the generation of mucosal CTL, and which acts through a secondary mechanism. To address this question, IFNγ$^{-/-}$ mice (BALB/c background) and conventional BALB/c mice were treated with the rmIL-12 (I μg/mouse)+ DOTAP IR together with peptide. Mucosal treatment of IR-immunized IFNγ$^{-/-}$ mice with rmIL-12 did not lead to the induction of mucosal or systemic CTL (FIG. 17). It thus appears that IL-12 cannot act directly in the induction of mucosal CD8$^+$ CTL in the absence of IFNγ.

In summary, the foregoing Examples incorporate a novel viral challenge system in which recombinant vaccinia virus expressing HIV-1 gp160 is used as a surrogate for HIV-1, since we cannot infect the mice with HIV-1. Importantly, in this system, neutralizing antibodies to gp160 cannot protect against recombinant vaccinia expressing gp160, because the virus does not incorporate gp160 in the virus particle but expresses it only in the infected cell. Thus, the protective immune response must be directed at the infected cell.

The results herein demonstrate that the protective response is completely dependent on CD8$^+$ cells., by the abrogation of protection after in vivo depletion of CD8$^+$ cells. Thus, the results show unequivocally that it is CD8$^+$ CTL (whether via lytic activity or via secretion of cytokines or other soluble factors) that protect. Since it has been shown that protection against vaccinia infection can be mediated by interferon-γ which is secreted by CD8$^+$ CTL in response to antigen stimulation (Harris et al., *J. Virol.* 69:910–915 (1995)), it is possible that the mechanism involves local secretion of this cytokine by the CTL rather than lysis of infected cell. By either mechanism, the CTL are responsible for mediating protection.

However, since the mucosal immunization induces CTL in both the local mucosal site and the spleen, this result does not distinguish which CTL are responsible for protection. To address this important question, the present Examples take advantage of the fact that subcutaneous immunization with the peptide vaccine induces systemic CTL in the spleen at a level at least as high as that induced by mucosal immunization, but does not induce mucosal CTL. Splenic CTL resulting from both immunization routes kill target cells endogenously expressing HIV-1 gp160. Thus, if systemic CTL against this epitope protected against mucosal challenge, then the subcutaneously immunized mice would have been expected to be protected.

However, the subcutaneously immunized mice showed no evidence of protection against mucosal challenge. Thus, the protection correlated with CrL activity in the local mucosal sites, Peyer's patches and lamina propria, not with CTL activity in the spleen. The protection was not only mediated by CTL, but also required CTL in the local mucosal site of challenge. Systemic CTL were not sufficient.

Protection mediated by local mucosal CTL appears independently sufficient to mediate a protective immune response. This conclusion is supported by the observation that a two-log reduction in viral pfu occurs in the ovary even at day 2 after mucosal viral challenge (from 2.37×10$^6$ pfu in unimmunized mice to 3.34×10$^4$ pfu in IR immunized mice), before much replication could have occurred in the ovary. This finding indicates that the reduction in titer in the ovary reflects a reduction in the amount of virus that can escape the initial mucosal site of infection. In addition, the enhancement of CTL activity and protection by rmIL-12 depended on local mucosal administration of the cytokine, not systemic administration.

One possible difference between CTL induced by mucosal versus systemic immunization is that the CTL resulting from the SC immunization do not have homing receptors for the GI mucosa, as evidenced by the fact that they are not detected in the lamina propria or Peyer's patches.

The present disclosure represents the first demonstration of protection against GI mucosal challenge requiring local mucosal CTL at the site of challenge. These results have important implications for the development of protective vaccines against mucosal exposure to viruses.

In addition to these results, the Examples provided herein also demonstrate a surprising persistence, not only of memory CTL in the mucosa, but also of protective immunity against mucosal viral challenge. Factors controlling CTL memory, and the role of persistent antigen in maintaining memory CTL, represent another issue that has been of interest for some time (Ahred and Gray, *Science* 272:54–60 (1996); Kundig et al., *Proc. Natl. Acad. Sci. U.S.A.* 93:9716–9723 (1996); Ehl et al., *Eur. J. Immunol.* 27:3404–3413 (1997)), but has been little studied in the context of mucosal immune responses and protection. In studies of systemic immunity, it was shown (Slifka et al., *Blood* 90:2103–2108, (1997)) that after infection with lymphocytic choriomeningitis virus (LCMV), CTL memory responses were present in the bone marrow for at least 325 days, indicating long-term persistence of antiviral T cells at this site. While the antigen-specific CD8$^+$ T cell number dropped precipitously following viral clearance, substantial numbers persisted for the life of the mouse (Muraii-Krishna et al., *Immunity* 8:177–187, (1998)). Upon rechallenge with LCMV, there was rapid expansion of memory CD8$^+$ T cells.

These results indicate that systemic infection with virus can lead to long-term memory and protection. In the case of mucosal CTL memory, it was shown that memory CTL remained at the mucosal site longer if the immunization was via the mucosal route (Gallichan and Rosenthal, *J. Exp. Med.* 184:1879–1890 (1996)), but the duration of protection by such mucosal CTL was not studied. The ability of mucosal memory CTL to protect will depend in part on the rapidity by which they can expand and be activated after virus exposure, which may relate to the level of virus replication in the mucosal site. For these reasons, it is important to determine the duration of mucosal protection dependent on local mucosal $CD8^+$ CTL. The results herein show persistence of CTL even six months after mucosal immunization with the peptide vaccine construct, without additional reimmunization beyond the initial three-week course. This response is accompanied by protection against mucosal challenge with vaccinia virus expressing gp160.

This latter result is particularly striking because the exemplary immunogen is a peptide administered without any depot form of adjuvant that would maintain the presence of antigen for extended periods. It would be expected that free peptide delivered to the lumen of the gut, or even after transport by mucosal cells, would have a very short half-life. Therefore, either memory CTL can persist in the mucosa at levels sufficient to mediate protection in the absence of persistent antigen, or antigen must persist locally in some cell-bound form, perhaps on N4HC molecules of dendritic cells. Yet another possibility is that the peptide crossreacts with one of the antigens in the mucosal flora and that these crossreactive antigens maintain the memory CTL.

Protection against viral infection by CTL involves more than just the number of CTL induced. Quality of CTLs is as important for in vivo protection as quantity. Previous reports have shown that high-avidity P18IIIB-specific CTLs adoptively transferred into severe combined immunodeficient (SCID) mice were 100- to 1000-fold more effective at viral clearance than the low-avidity CTLs specific for the same peptide-MHC complex, despite the fact that all CTL lines lysed virus infected targets in vitro (Alexander-Miller et al., *Proc. Natl. Acad. Sci. U.S.A.* 93:4102–4107 (1996)). Thus, the CTL induced by mucosal immunization with the synthetic peptide vaccine must be present not only in sufficient quantity to protect, but also must be of high enough avidity to protect.

Other aspects of the present disclosure enable optimization of induction of the CTL response and protective immunity. Delivery of certain cytokines such as IL-12 at the site of antigen immunization systemically have been shown to enhance systemic CTL responses (Ahlers et al., *J. Immunol.* 159:3947–3958 (1997); Iwasaki et al., *J. Immunol.* 159:4591–4601 (1997); Xiang and Ertl, *Immunity* 2:129–135 (1995); Irvine et al., *J. Immunol.* 156:238–245 (1996)). However, no comparable studies have been conducted for mucosal CTL responses.

In the model system disclosed herein, induction of mucosal CTL is dependent on endogenous production of IL-12 by the mouse, because it could be inhibited by anti-IL-12 antibody given in vivo before and after each immunization. In the present Examples, IL-12 co-administered with the antigen intrarectally significantly enhanced CTL induction, and also increased protection against intrarectal vaccinia viral challenge. However, it was striking that IL-12 delivered systemically (i.p.) did not enhance CTL induction either in the systemic sites (eg. spleen) or in the mucosa. This difference may be due to the short half life of IL-12 delivered systemically, which prevented it from surviving long enough to get to the sites of CTL induction. Therefore, for mucosal CTL induction as well as for systemic CTL induction, it is important to deliver the cytokine directly to the site of antigen administration and CTL induction.

Enhancement of CTL induction in the mucosa with recombinant IL-12 is a useful strategy for mucosal vaccine development. In this context, small doses given locally in the mucosal sites are not likely to have the global toxicity that has been associated with systemic administration of this cytokine.

The results herein further show that enhancement of the CTL response in vivo by rmIL-12 is dependent on interferon-$\gamma$, as no enhancement was observed in IFN$\gamma^{-/-}$ mice. At least two mechanisms can explain this result. First, IL-12 may be acting through its well-defined ability to induce production of IFN$\gamma$ (Trinchieri, G., *Blood* 94:4008–4027 (1994)), which then acts directly on CTL precursors. Alternatively, since IFN$\gamma$ is important for expression of the IL-12 receptor (Szabo, et al., *J. Exp. Med.* 185:817–824 (1997)) IL-12 may act directly on CTL, but may not be able to act in IFN$\gamma^{-/-}$ mice because of the lack of IL-12R expression.

There is evidence that CTL activity may play a role in protective immunity in humans against HIV-1 (reviewed in (Rowland-Jones et al., *Adv. Immunol.* 65:277–346 (1997); Yang, O.O. and B. D. *Walker, Adv. Immunol.* 66:273–311 (1997); Berzofsky and Berkower, *AIDS* 9(A):S 143-S 157 (1995)). Cell-mediated immunity to HIV-1 has been demonstrated in uninfected high risk adults (Pinto et al., *J. Clin. Invest.* 96:867–876, (1995); Rowland-Jones et al., *Nature Medicine* 1:59–64, (1995)) and in uninfected children born to infected mothers (Clerici et al., *AIDS* 7:1427–1433 (1993); Luzuriaga and Sullivan, *J. Cell. Blochem. Supplement* 17E:98.(Abstract) (1993)). CTL activity has been correlated with low viral load and long-term non-progressor status in some infected individuals (Cao et al., *N. Enal. J. Med.* 332:201–208 (1995)). CTL have also been associated with recovery from acute HIV or SIV infection (Yasutomi et al., *J. Virol.* 67:1707–1711 (1993); Reimann et al., *J. Virol.* 68:2362–2370 (1994); Koup et al. *J. Virol.* 68:4650–4655 (1994); Borrow et al., *Nature Medicine* 3:205–211, (1997)). Induction of escape mutations by CTL implies that the CTL are eliminating the bulk of the wild type virus (Borrow et al., *Nature Medicine* 3:205–211 (1997); Phillips et al., *Nature* 354:453–459 (1991); Nowak et al., *Nature* 375:606–611 (1995); Goulder et al., *Nature Medicine* 3:212–217 (1997); Couillin et al., *J. Exp. Med.* 180:1129–1134 (1994); Koenig et al., *Nature Medicine* 1:330–336 (1995)). In addition, in an SIV study, protection was associated with a particular simian class I MHC molecule (Heeney et al., *J. Exp. Med.* 180:769–774, (1994)). $CD8^+$ cells have been demonstrated to suppress replication of human and simian lentiviruses in autologous CD4 cells by a non-lytic mechanism involving soluble factors synthesized and released by activated $CD8^+$ cells (Walker et al., *Science* 234:1563–1566 (1986); Tsubota et al., *J. Exp. Med.* 169:1421–1434 (1989); Walker and Levy, *Immunology* 66:628–630 (1989); Mackewicz et al., *J. Clin. Invest.* 87:1462–1466, (1991); van Kuyk et al., *J. Immunol.* 153:4826–4833 (1994)). Such soluble factors include the chemokines RANTES, MIP-1$\alpha$, and MIP-1$\beta$ (Cocchi et al., *Science* 270:1811–1815 (1995)).

The present disclosure provides the first demonstration of protection against mucosal viral challenge mediated by CTL, which must be present in the local mucosa. Also provided are methods and compositions for enhancing the; induction of such local mucosal CTL by a peptide vaccine given together with recombinant IL-12 at the mucosal site. These methods and compositions for stimulating CTL immunity at local sites of mucosal exposure represent important tools for vaccine development to prevent HIV infection or disease in humans. Because the gastrointestinal tract appears to be a major site of early SIV and HIV replication, among other pathogens, and because this and other mucosal sites are frequent sites of entry for these pathogens, it is particularly critical to achieve protection at mucosal sites. The present disclosure satisfies these objects and provides other advantages as set forth above.

Although the invention has been described with reference to the presently preferred embodiment, it should be understood that various modifications can be made without departing from the spirit of the invention. Accordingly, the invention is limited only by the following claims.

What is claimed is:

1. A method for inducing an antigen specific systemic and rectal mucosal cytotoxic T lymphocyte (CTL) response in a mammalian subject comprising contacting a rectal mucosal tissue of the subject with a composition comprising a chimeric peptide having the amino acid sequence KQIINMWQEVGKAMYAPPISGQIRIQRGPGRAFVTIGK (SEQ ID NO: 2).

2. The method of claim 1, wherein said composition further comprises an adjuvant.

3. The method of claim 2, wherein the adjuvant is selected from cholera toxin (CT), mutant cholera toxin (MCT), or mutant-*E. coli* heat labile enterotoxin (MLT).

4. The method of claim 1, further comprising administering a purified cytokine to the subject.

5. The method of claim 4, wherein the cytokine is contacted with the rectal mucosal surface.

6. The method of claim 4, wherein the purified cytokine is selected from granulocyte-macrophage colony-stimulating factor (GM-CSF), interleukin-2 (IL-2), interlukin-7 (IL-7), interleukin-12 (IL-12) or tumor necrosis factor a (TNFa).

7. The method of claim 1, further comprising administering purified interferon-γ to the subject.

8. The method of claim 7, wherein the purified interferon-γ is contacted with the rectal mucosal surface of the subject.

9. The method of claim 4, further comprising administering purified interferon-γ to the subject.

10. The method of claim 9, wherein the purified interferon-γ is contacted with the rectal mucosal surface of the subject.

11. The method of claim 1, wherein said composition further comprises a purified cytokine selected from granulocyte-macrophage colony-stimulating factor (GM-CSF), interleukin-2 (IL-2), interleukin-7 (IL-7), interleukin-12 (IL-12) or tumor necrosis factor.

12. The method of claim 1, wherein said composition further comprises purified interferon-γ.

13. The method of claim 11, wherein said composition further comprises purified interferon-γ.

14. A method for inducing an antigen specific systemic and rectal mucosal CTL response in a mammalian subject, comprising contacting a rectal mucosal tissue of the subject with a composition comprising a chimeric peptide having the amino acid sequence KQIINMWQEVGKAMYAPPISGQIRRIQRGPGR AFVTIGK (SEQ ID NO: 2), wherein said composition does not comprise an adjuvant.

15. The method of claim 14, further comprising administering a purified cytokine the subject.

16. The method of claim 15, wherein the cytokine is contacted with the rectal mucosal surface of the subject.

17. The method of claim 16, wherein the purified cytokine is selected from granulocyte-macrophage colony-stimulating factor (GM-CSF, interleukin-2 (IL-2), interleukin-7 (IL-7), interleukin-12 (IL-12) or tumor necrosis factor a (TNFa).

18. The method of claim 14, further comprising administering purified interferon-γ to the subject.

19. The method of claim 18, wherein the purified interferon-γ is contacted with a mucosal surface of the subject.

20. The method of claim 15, further comprising administering purified interferon-γ to the subject.

21. The method of claim 20, wherein the purified interferon-γ is contacted with a mucosal surface of the subject.

22. The method of claim 14, wherein said composition further comprises a purified cytokine selected from granulocyte-macrophage colony-stimulating factor (GM-CSF), interleukin-2 (IL-2), interleukin-7 (IL-7), interleukin-12 (IL-12) or tumor necrosis factor.

23. The method of claim 14, wherein said composition further comprises purified interferon-γ.

24. The method of claim 22, wherein said composition further comprises purified interferon-γ.

25. An immunogenic composition comprising a chimeric peptide having the amino acid sequence KQITNMWQEVGKAMYAPPISGQIRRIQRGPGRAFVTIGK (SEQ ID NO: 2), formulated for intrarectal delivery to the rectum, colon, sigmoid colon, or distal colon; wherein said composition is formulated as a rectal emulsion, foam, suppository, or gel preparation and comprises a base, carrier, or absorption-promoting agent adapted for intrarectal delivery.

26. The immunogenic composition of claim 25, wherein the chimeric peptide is admixed with a rectally-compatible homogeneous gel carrier.

27. The immunogenic composition of claim 26, wherein the homogenous gel carrier is a polyoxyethylene gel.

28. The immunogenic composition of claim 25, wherein the suppository is comprised of a base selected from a polyethyleneglycol, witepsol H15, witepsol W35, witepsol E85, propyleneglycol dicaprylate (Sefsol 228), Miglyol 810, hydroxypropylcellulose-H (HPC), or carbopol-934P (CP).

29. The immunogenic composition of claim 28, comprising at least two base materials.

30. The immunogenic composition of claim 25, further comprising a stabilizing agent to minimize intrarectal degradation of the chimeric peptide.

31. The immunogenic composition of claim 25, wherein the absorption-promoting agent is selected from a surfactant, mixed micelle, enamines, nitric oxide donor, sodium salicylate, glycerol ester of acetoacetic acid, clyclodextrin or beta-cyclodextrin derivative, or medium-chain fatty acid.

32. The immunogenic composition of claim 25, further comprising an adjuvant.

33. The immunogenic composition of claim 32, wherein the adjuvant is selected from cholera toxin (CT), mutant cholera toxin (MCT), mutant-*E. coli* heat labile enterotoxin, or pertussis toxin.

34. The immunogenic composition of claim 32, wherein the adjuvant is conjugated to a mucosal tissue or T cell binding agent.

35. The immunogenic composition of claim 34, wherein the mucosal tissue or T cell binding agent is selected from protein A, an antibody that binds a mucosal tissue- or T-cell-specific protein, or a ligand or peptide that binds a mucosal tissue- or T-cell-specific protein.

36. The immunogenic composition of claim 32, wherein the adjuvant comprises a recombinant cholera toxin (CT) having a B chain of CT substituted by protein A conjugated to a CT A chain.

37. The immunogenic composition of claim 32, wherein the adjuvant is conjugated to a protein or peptide that binds specifically to T cells.

38. The immunogenic composition of claim 32, further comprising purified IL-12.

39. The immunogenic composition of claim 32, further comprising purified interferon-γ.

40. The immunogenic composition of claim 39, further comprising purified IL-12.

* * * * *

```
                              SEQUENCE LISTING

<160> NUMBER OF SEQ ID NOS:  20

<210> SEQ ID NO 1
<211> LENGTH: 35
<212> TYPE: PRT
<213> ORGANISM: Human immunodeficiency virus type 1

<400> SEQUENCE: 1

Glu Gln Met His Glu Asp Ile Ile Ser Leu Trp Asp Gln Ser Leu Lys
  1               5                  10                  15

Pro Cys Val Lys Arg Ile Gln Arg Gly Pro Gly Arg Ala Phe Val Thr
                 20                  25                  30

Ile Gly Lys
        35

<210> SEQ ID NO 2
<211> LENGTH: 39
<212> TYPE: PRT
<213> ORGANISM: Human immunodeficiency virus type 1

<400> SEQUENCE: 2

Lys Gln Ile Ile Asn Met Trp Gln Glu Val Gly Lys Ala Met Tyr Ala
  1               5                  10                  15

Pro Pro Ile Ser Gly Gln Ile Arg Arg Ile Gln Arg Gly Pro Gly Arg
                 20                  25                  30

Ala Phe Val Thr Ile Gly Lys
        35

<210> SEQ ID NO 3
<211> LENGTH: 39
<212> TYPE: PRT
<213> ORGANISM: Human immunodeficiency virus type 1

<400> SEQUENCE: 3

Arg Asp Asn Trp Arg Ser Glu Leu Tyr Lys Tyr Lys Val Val Lys Ile
  1               5                  10                  15

Glu Pro Leu Gly Val Ala Pro Thr Arg Ile Gln Arg Gly Pro Gly Arg
                 20                  25                  30

Ala Phe Val Thr Ile Gly Lys
        35

<210> SEQ ID NO 4
<211> LENGTH: 48
<212> TYPE: PRT
<213> ORGANISM: Human immunodeficiency virus type 1

<400> SEQUENCE: 4

Ala Val Ala Glu Gly Thr Asp Arg Val Ile Glu Val Val Gln Gly Ala
  1               5                  10                  15

Tyr Arg Ala Ile Arg His Ile Pro Arg Arg Ile Arg Gln Gly Leu Glu
                 20                  25                  30
```

Arg Arg Ile Gln Arg Gly Pro Gly Arg Ala Phe Val Thr Ile Gly Lys
            35                  40                  45

<210> SEQ ID NO 5
<211> LENGTH: 42
<212> TYPE: PRT
<213> ORGANISM: Human immunodeficiency virus type 1

<400> SEQUENCE: 5

Asp Arg Val Ile Glu Val Val Gln Gly Ala Tyr Arg Ala Ile Arg His
 1               5                  10                  15

Ile Pro Arg Arg Ile Arg Gln Gly Leu Glu Arg Ile Gln Arg Gly
            20                  25                  30

Pro Gly Arg Ala Phe Val Thr Ile Gly Lys
        35                  40

<210> SEQ ID NO 6
<211> LENGTH: 30
<212> TYPE: PRT
<213> ORGANISM: Human immunodeficiency virus type 1

<400> SEQUENCE: 6

Asp Arg Val Ile Glu Val Val Gln Gly Ala Tyr Arg Ala Ile Arg Arg
 1               5                  10                  15

Ile Gln Arg Gly Pro Gly Arg Ala Phe Val Thr Ile Gly Lys
            20                  25                  30

<210> SEQ ID NO 7
<211> LENGTH: 32
<212> TYPE: PRT
<213> ORGANISM: Human immunodeficiency virus type 1

<400> SEQUENCE: 7

Ala Gln Gly Ala Tyr Arg Ala Ile Arg His Ile Pro Arg Ile Arg
 1               5                  10                  15

Arg Ile Gln Arg Gly Pro Gly Pro Arg Ala Phe Val Thr Ile Gly Lys
            20                  25                  30

<210> SEQ ID NO 8
<211> LENGTH: 35
<212> TYPE: PRT
<213> ORGANISM: Human immunodeficiency virus type 1

<400> SEQUENCE: 8

Glu Gln Met His Glu Asp Ile Ile Ser Leu Trp Asp Gln Ser Leu Lys
 1               5                  10                  15

Pro Cys Val Lys Arg Ile His Ile Gly Pro Gly Arg Ala Phe Tyr Thr
            20                  25                  30

Thr Lys Asn
        35

<210> SEQ ID NO 9
<211> LENGTH: 39
<212> TYPE: PRT
<213> ORGANISM: Human immunodeficiency virus type 1

<400> SEQUENCE: 9

Lys Gln Ile Ile Asn Met Trp Gln Glu Val Gly Lys Ala Met Tyr Ala
 1               5                  10                  15

Pro Pro Ile Ser Gly Gln Ile Arg Arg Ile His Ile Gly Pro Gly Arg
            20                  25                  30

Ala Phe Tyr Thr Thr Lys Asn
         35

<210> SEQ ID NO 10
<211> LENGTH: 39
<212> TYPE: PRT
<213> ORGANISM: Human immunodeficiency virus type 1

<400> SEQUENCE: 10

Arg Asp Asn Trp Arg Ser Glu Leu Tyr Lys Tyr Lys Val Val Lys Ile
 1               5                  10                  15

Glu Pro Leu Gly Val Ala Pro Thr Arg Ile His Ile Gly Pro Gly Arg
             20                  25                  30

Ala Phe Tyr Thr Thr Lys Asn
         35

<210> SEQ ID NO 11
<211> LENGTH: 48
<212> TYPE: PRT
<213> ORGANISM: Human immunodeficiency virus type 1

<400> SEQUENCE: 11

Ala Val Ala Glu Gly Thr Asp Arg Val Ile Glu Val Val Gln Gly Ala
 1               5                  10                  15

Tyr Arg Ala Ile Arg His Ile Pro Arg Arg Ile Arg Gln Gly Leu Glu
             20                  25                  30

Arg Arg Ile His Ile Gly Pro Gly Arg Ala Phe Tyr Thr Thr Lys Asn
         35                  40                  45

<210> SEQ ID NO 12
<211> LENGTH: 42
<212> TYPE: PRT
<213> ORGANISM: Human immunodeficiency virus type 1

<400> SEQUENCE: 12

Asp Arg Val Ile Glu Val Val Gln Gly Ala Tyr Arg Ala Ile Arg His
 1               5                  10                  15

Ile Pro Arg Arg Ile Arg Gln Gly Leu Glu Arg Arg Ile His Ile Gly
             20                  25                  30

Pro Gly Arg Ala Phe Tyr Thr Thr Lys Asn
         35                  40

<210> SEQ ID NO 13
<211> LENGTH: 30
<212> TYPE: PRT
<213> ORGANISM: Human immunodeficiency virus type 1

<400> SEQUENCE: 13

Asp Arg Val Ile Glu Val Val Gln Gly Ala Tyr Arg Ala Ile Arg Arg
 1               5                  10                  15

Ile His Ile Gly Pro Gly Arg Ala Phe Tyr Thr Thr Lys Asn
             20                  25                  30

<210> SEQ ID NO 14
<211> LENGTH: 31
<212> TYPE: PRT
<213> ORGANISM: Human immunodeficiency virus type 1

<400> SEQUENCE: 14

Ala Gln Gly Ala Tyr Arg Ala Ile Arg His Ile Pro Arg Arg Ile Arg
 1               5                  10                  15

-continued

Arg Ile His Ile Gly Pro Gly Arg Ala Phe Tyr Thr Thr Lys Asn
                20                  25                  30

<210> SEQ ID NO 15
<211> LENGTH: 15
<212> TYPE: PRT
<213> ORGANISM: Human immunodeficiency virus type 1

<400> SEQUENCE: 15

Arg Ile Gln Arg Gly Pro Gly Arg Ala Phe Val Thr Ile Gly Lys
 1               5                  10                  15

<210> SEQ ID NO 16
<211> LENGTH: 10
<212> TYPE: PRT
<213> ORGANISM: Human immunodeficiency virus type 1

<400> SEQUENCE: 16

Arg Gly Pro Gly Arg Ala Phe Val Thr Ile
 1               5                  10

<210> SEQ ID NO 17
<211> LENGTH: 20
<212> TYPE: PRT
<213> ORGANISM: Human immunodeficiency virus type 1

<400> SEQUENCE: 17

Glu Gln Met His Glu Asp Ile Ile Ser Leu Trp Asp Gln Ser Leu Lys
 1               5                  10                  15

Pro Cys Val Lys
            20

<210> SEQ ID NO 18
<211> LENGTH: 24
<212> TYPE: PRT
<213> ORGANISM: Human immunodeficiency virus type 1

<400> SEQUENCE: 18

Lys Gln Ile Ile Asn Met Trp Gln Glu Val Gly Lys Ala Met Tyr Ala
 1               5                  10                  15

Pro Pro Ile Ser Gly Gln Ile Arg
            20

<210> SEQ ID NO 19
<211> LENGTH: 24
<212> TYPE: PRT
<213> ORGANISM: Human immunodeficiency virus type 1

<400> SEQUENCE: 19

Arg Asp Asn Trp Arg Ser Glu Leu Tyr Lys Tyr Lys Val Val Lys Ile
 1               5                  10                  15

Glu Pro Leu Gly Val Ala Pro Thr
            20

<210> SEQ ID NO 20
<211> LENGTH: 33
<212> TYPE: PRT
<213> ORGANISM: Human immunodeficiency virus type 1

<400> SEQUENCE: 20

```
Ala Val Ala Glu Gly Thr Asp Arg Val Ile Glu Val Val Gln Gly Ala
  1               5                  10                 15

Tyr Arg Ala Ile Arg His Ile Pro Arg Arg Ile Arg Gln Gly Leu Glu
               20                  25                  30

Arg
```